(12) United States Patent
Rougeot

(10) Patent No.: US 8,889,827 B2
(45) Date of Patent: Nov. 18, 2014

(54) OPIORPHIN PEPTIDE DERIVATIVES AS POTENT INHIBITORS OF ENKEPHALIN-DEGRADING ECTOPEPTIDASES

(75) Inventor: Catherine Rougeot, Chevreuse (FR)

(73) Assignee: Institut Pasteur, Paris (FR)

( * ) Notice: Subject to any disclaimer, the term of this patent is extended or adjusted under 35 U.S.C. 154(b) by 576 days.

(21) Appl. No.: 12/936,591

(22) PCT Filed: Apr. 7, 2009

(86) PCT No.: PCT/EP2009/054171
§ 371 (c)(1),
(2), (4) Date: Dec. 22, 2010

(87) PCT Pub. No.: WO2009/124948
PCT Pub. Date: Oct. 15, 2009

(65) Prior Publication Data
US 2011/0124571 A1    May 26, 2011

Related U.S. Application Data

(60) Provisional application No. 61/042,922, filed on Apr. 7, 2008.

(51) Int. Cl.
*C07K 7/00* (2006.01)

(52) U.S. Cl.
USPC ......... 530/330; 514/21.8; 514/18.3; 514/20.1

(58) Field of Classification Search
USPC .................. 530/330; 514/21.8, 18.3, 20.1
IPC .................... C07K 7/00; A61K 38/08
See application file for complete search history.

(56) References Cited

U.S. PATENT DOCUMENTS

| | | | |
|---|---|---|---|
| 5,859,189 A | 1/1999 | Rosinski-Chupin et al. | |
| 6,025,143 A | 2/2000 | Rosinski-Chupin et al. | |
| 6,184,205 B1 | 2/2001 | Sparks et al. | |
| 6,589,750 B2 | 7/2003 | Rougeot et al. | |
| 6,818,405 B2 | 11/2004 | Rougeot et al. | |
| 6,916,607 B2 | 7/2005 | Rosinski-Chupin et al. | |
| 7,153,833 B2 | 12/2006 | Rougeot et al. | |
| 7,387,778 B2 | 6/2008 | Marcel et al. | |
| 7,423,020 B2 | 9/2008 | Rougeot et al. | |
| 7,429,448 B2 | 9/2008 | Rougeot et al. | |
| 7,625,713 B2 | 12/2009 | Rougeot et al. | |
| 2002/0019008 A1 | 2/2002 | Rougeot et al. | |
| 2002/0198361 A1 | 12/2002 | Rougeot et al. | |
| 2003/0186870 A1 | 10/2003 | Marcel et al. | |
| 2003/0195155 A1 | 10/2003 | Rougeot et al. | |
| 2004/0092486 A1 | 5/2004 | Rougeot et al. | |
| 2004/0116342 A1 | 6/2004 | Rougeot et al. | |
| 2005/0153374 A1 | 7/2005 | Rosinski-Chupin et al. | |
| 2007/0054861 A1 | 3/2007 | Rougeot et al. | |
| 2008/0206230 A1 | 8/2008 | Rougeot et al. | |
| 2009/0253639 A1 | 10/2009 | Rougeot | |
| 2009/0298109 A1 | 12/2009 | Rougeot | |
| 2010/0041072 A1 | 2/2010 | Rougeot et al. | |

FOREIGN PATENT DOCUMENTS

| | | |
|---|---|---|
| EP | 1216707 B1 | 2/2005 |
| EP | 1 577 320 A1 | 9/2005 |
| WO | 98 37100 | 8/1998 |
| WO | 02 051435 | 7/2002 |
| WO | 2005 090386 | 9/2005 |
| WO | WO 2005/090386 A1 | 9/2005 |
| WO | 2008 096276 | 8/2008 |
| WO | 2009 090265 | 7/2009 |
| WO | WO 2009/150040 A2 | 12/2009 |
| WO | WO 2010/060995 A1 | 6/2010 |

OTHER PUBLICATIONS

Roques (Trends in Pharmacological Sciences 21(12), 475-483, 2000).*
Bevan E.G. (Journal of Hypertension 10(7), 607-613, 1992).*
Iyengar, Srinivas (Heart Failure Clinics, 1(1), 95-102, 2005).*
Catherine Rougeot, et al., "Selective processing of submandibular rat 1 protein at dibasic cleavage sites salivary and bloodstream secretion products", Eur. J. Biochem., 219, 1994, pp. 765-773.
U.S. Appl. No. 13/131,470, filed May 26, 2011, Rougeot, et al.
U.S. Appl. No. 13/102,367, filed May 6, 2011, Rougeot, et al.
U.S. Appl. No. 12/994,534, filed Nov. 24, 2010, Rougeot.
U.S. Appl. No. 07/499,276, filed Jul. 19, 1990, Rosinski-Chupin, et al.
U.S. Appl. No. 09/599,927, filed Jun. 22, 2000, Marcel, et al.
International Search Report issued Mar. 1, 2010 in Application No. PCT/EP2009/056390.
Anne Wisner, et al., "Human Opiorphin, a natural antinociceptive modulator of opioid-dependent pathways", Proceedings of the National Academy of Sciences of USA, vol. 103, No. 47, XP-002499569, Nov. 21, 2006, pp. 17979-17984.
International Search Report issued Sep. 8, 2009 in PCT/EP09/54171 filed Apr. 7, 2009.

* cited by examiner

*Primary Examiner* — David Lukton
(74) *Attorney, Agent, or Firm* — Law Office of Salvatore Arrigo and Scott Lee, LLP

(57) ABSTRACT

The present invention relates to modified opiorphin peptides as new inhibitors of metallo-ectopeptidases.

17 Claims, 17 Drawing Sheets

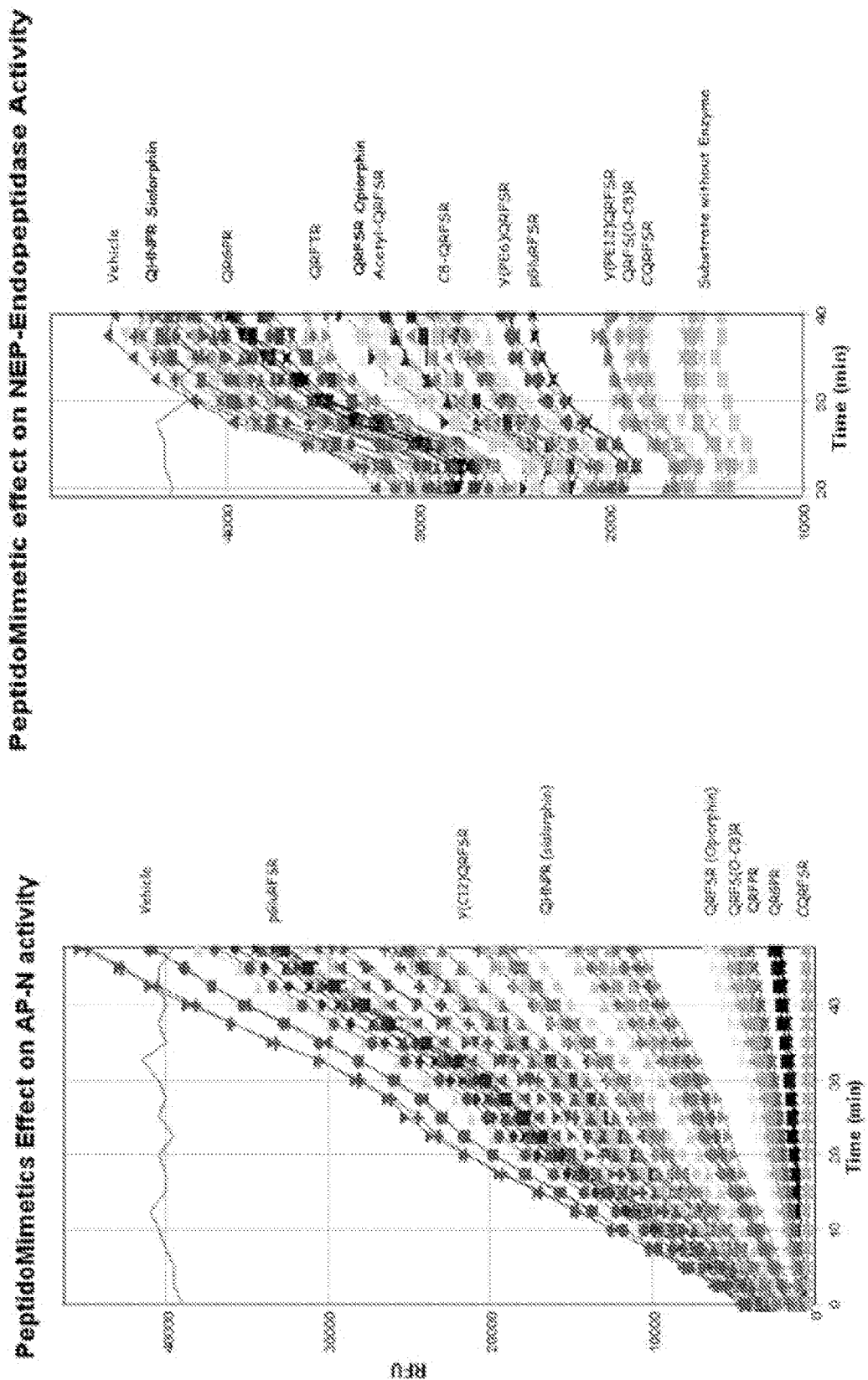

OPIORPHIN PEPTIDE DERIVATIVES AS POTENT INHIBITORS OF ENKEPHALIN-DEGRADING ECTOPEPTIDASES

The instant application is a national stage entry of PCT/EP09/54171, filed Apr. 7, 2009, which claims the benefit of U.S. provisional application Ser. No. 61/042,922 which was filed on Apr. 7, 2008, and which is incorporated by reference.

BACKGROUND OF THE INVENTION

1. Field of the Invention

The present invention relates to modified opiorphin peptides as new inhibitors of metallo-ectopeptidases.

2. Description of the Related Art

Zinc metal ectopeptidases control the receptor-dependent activity of neural and hormonal mediators involved in the regulation of important physiological functions in mammals. They are located at the surface of cells in nervous and systemic tissues and catalyze postsecretory processing or metabolism of neuropeptides and regulatory peptides (Rogues, B P, Noble, F, Dauge, V, Fournie-Zaluski, M C & Beaumont, A. (1993) *Pharmacol Rev* 45, 87-146. Turner, A J, Isaac, R E & Coates, D. (2001) *BioEssays* 23, 261-269).

Prominent among these neuronal and/or hormonal peptide signals are substance P (SP) and enkephalins, which are implicated in the receptor-dependent modulation of behavioral adaptive responses to stressful or threatening environmental stimuli. They notably regulate spinal processing of nociceptive information and analgesic mechanisms, emotional and/or motivational responses, anxiety, aggression, and neuroimmune inflammatory phenomena (Dickenson, A H. (1995) *Br J Anaesth* 75, 193-200. Sora, I, Takahashi, N, Funada, M, Ujike, H, Revay, R S, Donovan, D M, Miner, L L & Uhl, G R. (1997) *Proc Natl Acad Sci USA* 94, 1544-1549; Konig, M, Zimmer, A M, Steiner, H, Holmes, P V, Crawley, J N, Brownstein, M J & Zimmer, A. (1996) *Nature* 383, 535-538; Filliol, D, Ghozland, S, Chluba, J, Martin, M, Matthes, H W, Simonin, F, Befort, K, Gaveriaux-Ruff, C, Dierich, A & LeMeur, M, et al. (2000) *Nat Genet.* 25, 195-200).

Because of the physiological importance and the critical role of zinc ectopeptidases in modulating the functional potency of downstream neuronal and hormonal signals, it is essential to focus on what controls their activity and, as a consequence, the overall regulatory cascade. The discovery of upstream regulators of ectopeptidase activity also is exciting from physiopathological and therapeutic points of view because of the potential for developing new candidate drugs.

A brain-specific heptapeptide named spinorphin was isolated and characterized from bovine spinal cord based on its inhibitory activity toward enkephalin-degrading ectoenzymes, such as neutral endopeptidase (NEP; EC 3.4.24.11 [EC]) and aminopeptidase N (AP-N; EC 3.4.11.2 [EC]) (Nishimura, K & Hazato, T. (1993) *Biochem Biophys Res Commun* 194, 713-719; Yamamoto, Y, Ono, H, Ueda, A, Shimamura, M, Nishimura, K & Hazato, T. (2002) *Curr Protein Pept Sci* 3, 587-599). In addition, we characterized rat sialorphin, a peptide mediator involved in adaptation to environmental changes in rat. Rat sialorphin is an endocrine peptide signal whose expression is activated by androgen regulation and whose secretion is stimulated under adrenergic-mediated response to environmental stress in male rats. It is a physiological inhibitor of the membrane-anchored rat NEP activity and is a powerful inhibitor of pain sensation in rats (Rougeot, C, Rosinski-Chupin, I, Njamkepo, E & Rougeon, F. (1994) *Eur J Biochem* 219, 765-773; Rougeot, C, Vienet, R, Cardona, A, Le Doledec, L, Grognet, J M & Rougeon, F. (1997) *Am J Physiol* 273, R1309-R1320.; Rougeot, C, Rosinski-Chupin, I & Rougeon, F. (1998) in Biomedical Reviews eds. Chaldakov, G N & Mathison, R. (Bulgarian-American Center, Varna, Bulgaria,) Vol 9, pp. 17-32; Rosinski-Chupin, I, Huaulme, J F, Rougeot, C & Rougeon, F. (2001) *Endocrinology* 142, 4550-4559; Rougeot, C, Messaoudi, M, Hermitte, V, Rigault, A G, Blisnick, T, Dugave, C, Desor, D & Rougeon, F. (2003) *Proc Natl Acad Sci USA* 100, 8549-8554).

Previously we demonstrated that human Opiorphin native peptide (QRFSR-peptide) (SEQ ID NO: 1), the first characterized in human to date, is an efficient dual inhibitor of two enkephalin-inactivating ectopeptidases, neutral endopeptidase NEP (EC 3.4.24.11) and aminopeptidase AP-N (EC 3.4.11.2) (Wisner et al. *Proc Natl Acad Sci USA*, November 2006, 103(47): 17979-84).

Opiorphin peptide derivatives have been described previously, see, e.g., Wisner et al. *Proc Natl Acad Sci USA*, November 2006, 103(47): 17979-84 and has the basic peptide sequence as QRFSR (SEQ ID NO: 1).

Thus, this sequence and the sequence defined by the following formula may be modified: X1-X2-Arg-Phe-Ser-Arg (SEQ ID NO: 43), wherein X1 represents H atom or a Tyr amino acid, X2 represents Gln or Glp when X1 is H, or X2 represents Gln when X1 is Tyr or Cys. Preferred is QRFSR (SEQ ID NO: 1), YQRFSR (SEQ ID NO: 9), and/or CQRFSR (SEQ ID NO: 13) with QRFSR (SEQ ID NO: 1) most preferred. It is understood that Glp is pyroglutamate, Tyr or Y is Tyrosine, Gln or Q is glutamine, Arg or R is Arginine, Phe or F is Phenylalanine, Ser or S is Serine, and Cys or C for Cysteine. These peptides have been described in the international patent application published as WO2005090386.

SUMMARY OF THE INVENTION

The invention provides new Opiorphin derivatives and in vitro functional characterization by using highly selective biochemical assays.

BRIEF DESCRIPTION OF THE DRAWINGS

FIGS. 1-4 The kinetic of hydrolysis of corresponding FRET-peptide substrates by recombinant hNEP or hAP-N in the presence of vehicle or in the presence of 50 µM QRFSR-peptide (SEQ ID NO: 1) analogs. Each point represents the intensity of the signal expressed in RFU (Relative Fluorescence Unit), which was proportional to the quantity of metabolites formed, as function of reaction time (min). FIG. 1 discloses SEQ ID NOS 26, 11, 4, 1, 12, 38, 3 and 13, respectively, in order of appearance, FIG. 2 discloses SEQ ID NOS 4, 3, 54, 1, 5, 6, 10, 26, 11, 38 and 13, respectively, in order of appearance, FIG. 3 discloses SEQ ID NOS 1, 26 and 11-13, respectively, in order of appearance and FIG. 4 discloses SEQ ID NOS 3, 26, 1, 11, 38 and 13, respectively, in order of appearance.

FIG. 5 discloses SEQ ID NOS 2-4, 29 and 38, respectively, in order of appearance.

FIG. 6 discloses SEQ ID NOS 11, 10 and 9, respectively, in order of appearance.

FIG. 7 discloses SEQ ID NOS 13 and 25, respectively, in order of appearance and FIG. 8 discloses SEQ ID NOS 12, 6 and 5, respectively, in order of appearance.

FIGS. 12-15 disclose SEQ ID NO: 13 and FIGS. 16-17 disclose SEQ ID NO: 12.

DETAILED DESCRIPTION OF THE PREFERRED EMBODIMENTS

Figure 4:
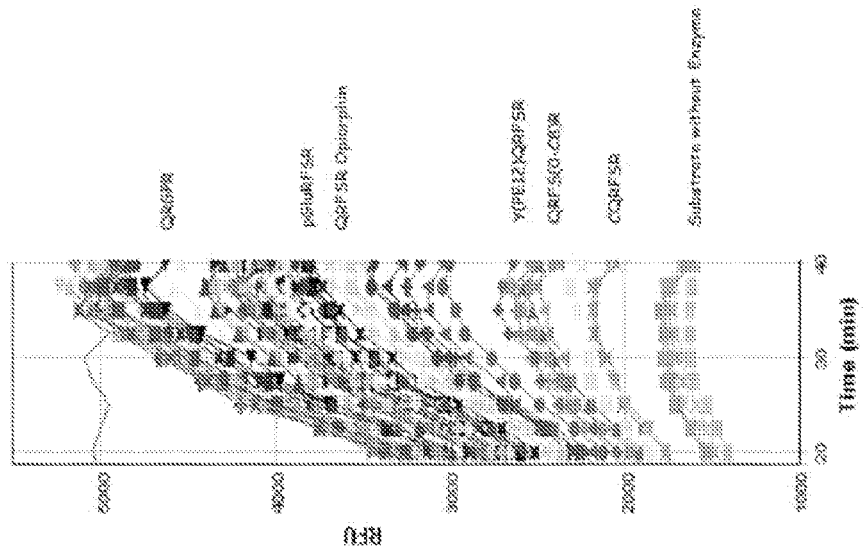
Figure 3:
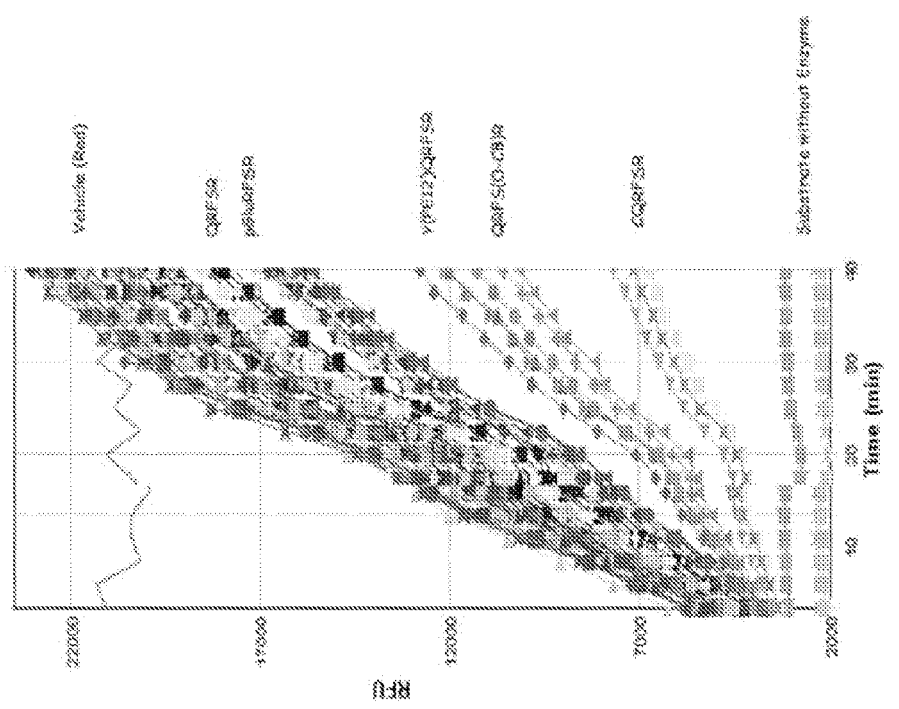
Figure 5:
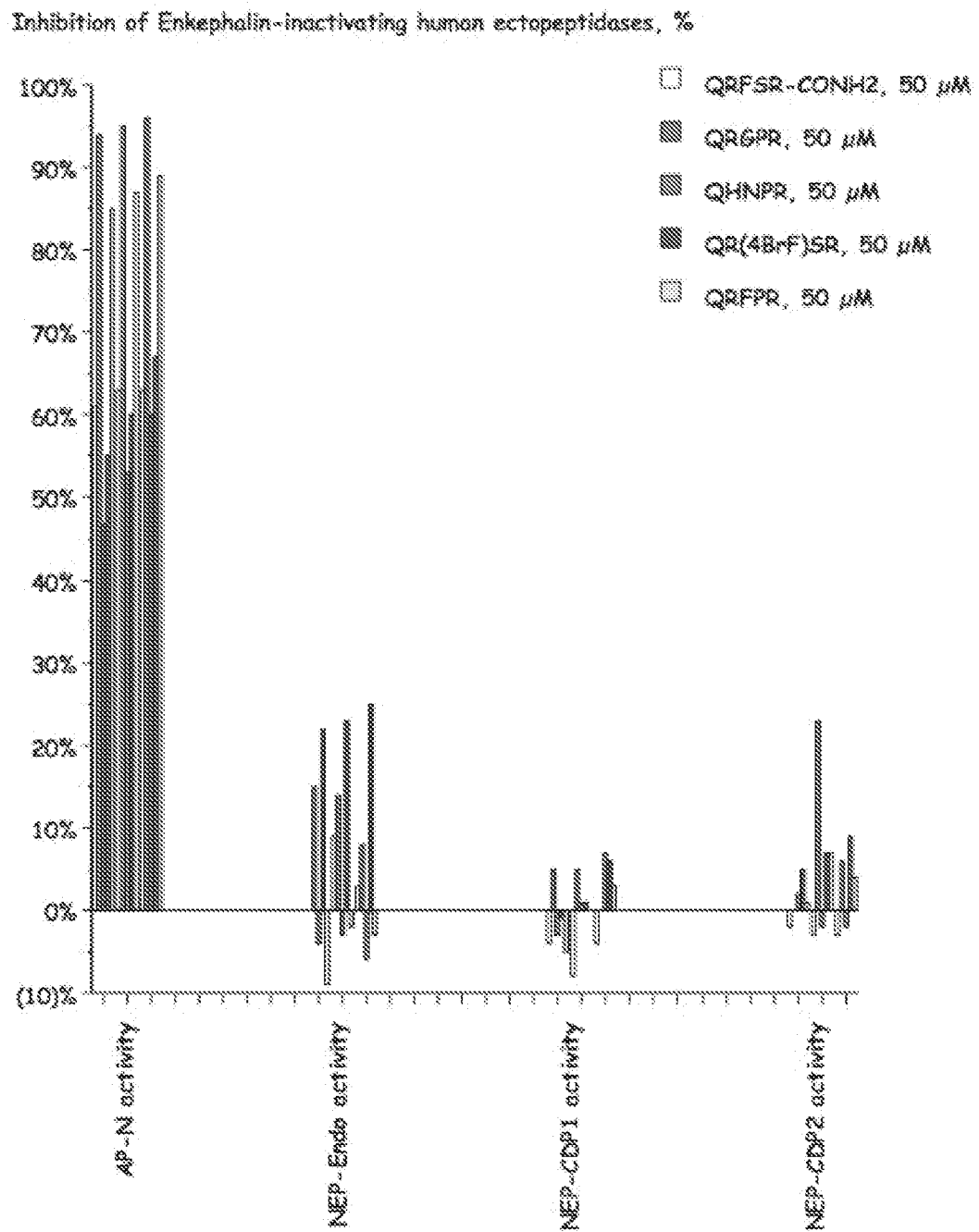
FIG. 5: Inhibition by QRFSR-peptide (SEQ ID NO: 1) analogs of hydrolysis of corresponding FRET-peptide substrates by pure recombinant human hNEP or AP-N. Each bar represents the percentage of intact substrate recovered and calculated as: percentage of velocity without inhibitor—velocity in presence of inhibitor/velocity without inhibitor, which was measured in the absence or in the presence of 50 µM of QRFSR-peptide (SEQ ID NO: 1) analogs.
Figure 6:
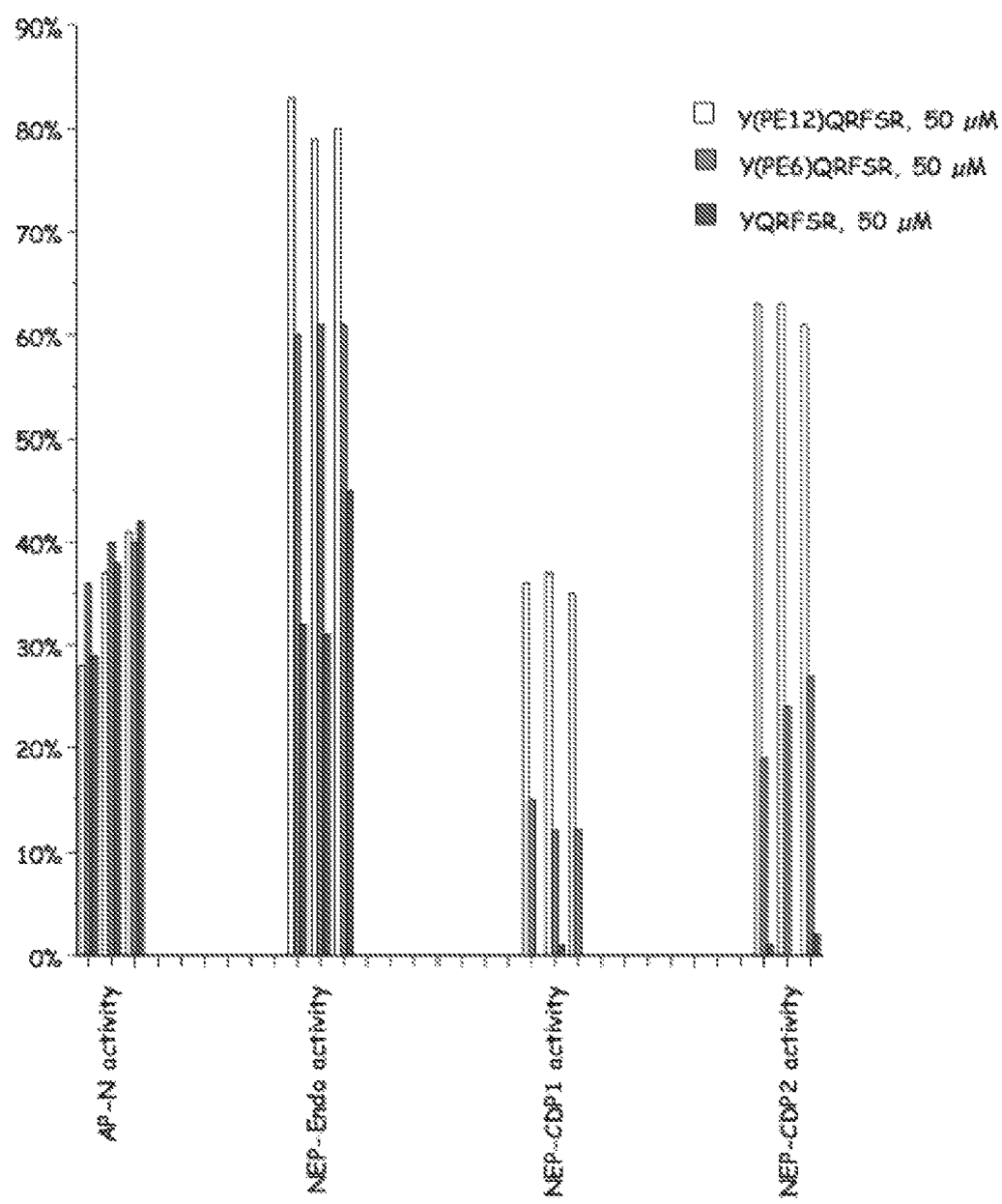
FIG. 6: substrates by pure recombinant human hNEP or AP-N. Each bar represents the percentage of intact substrate recovered and calculated as: percentage of velocity without inhibitor—velocity in presence of inhibitor/velocity without inhibitor, which was measured in the absence or in the presence of 50 µM of QRFSR-peptide (SEQ ID NO: 1) analogs.
Figure 7:
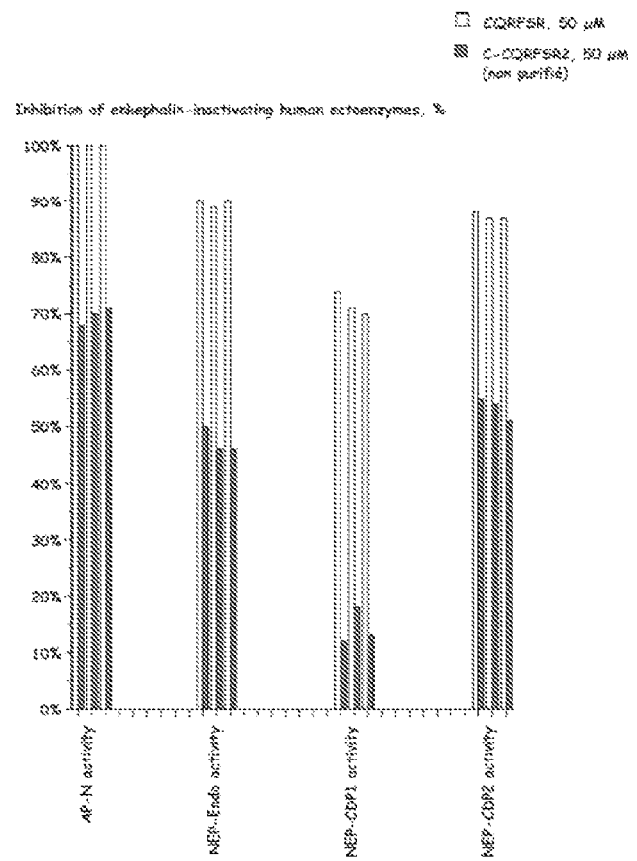
FIGS. 7-8: Inhibition by QRFSR-peptide (SEQ ID NO: 1) analogs of hydrolysis of corresponding FRET-peptide substrates by pure recombinant human hNEP or AP-N. Each bar represents the percentage of intact substrate recovered and calculated as: percentage of velocity without inhibitor—velocity in presence of inhibitor/velocity without inhibitor, which was measured in the absence or in the presence of 50 µM of QRFSR-peptide (SEQ ID NO: 1) analogs.
Figure 8:
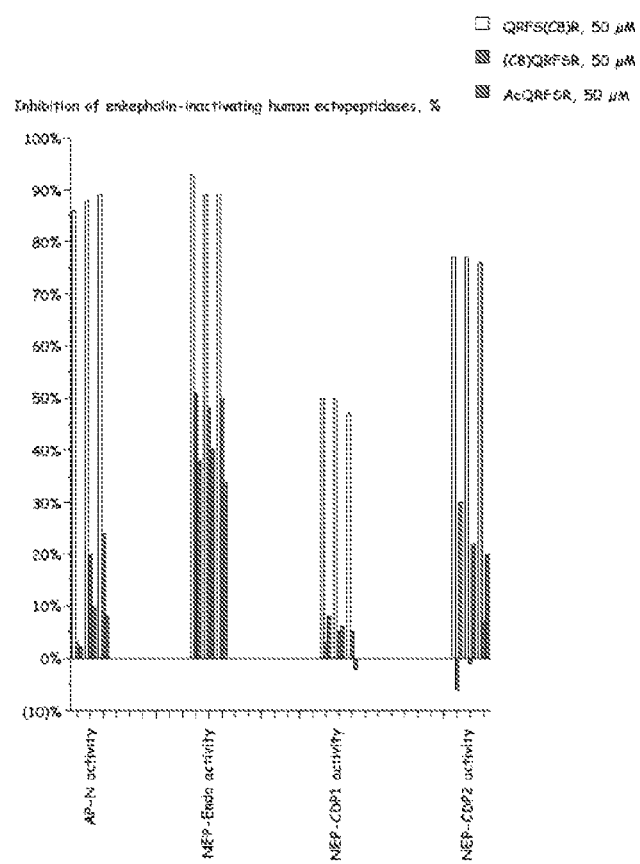

The invention here provides modified versions of these peptides where each or combinations of the amino acid residues that compose the opiorphin peptide are modified with one or more functional groups.

Non-limiting examples of such modified opiorphin peptides include:
NH2-QRFSR-CONH2 (SEQ ID NO: 2);
NH2-QRGPR-COOH (SEQ ID NO: 3);
NH2-QHNPR-COOH (SEQ ID NO: 4);

NH2-QR(4BromoF)SR—COOH (i.e. NH2-QR—F[4Br]-SR—COOH (SEQ ID NO: 29), wherein —F[4Br]— is a phenylalanine, the phenyl group of which is substituted in the para position by a bromo atom so that —F[4Br]— has the following formula:

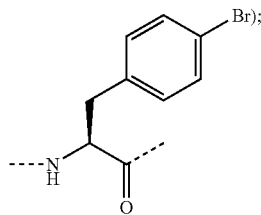

N-(Acetyl)QRFSR-COOH (SEQ ID NO: 5);
N—(C8-polyethylene)QRFSR-COOH (SEQ ID NO: 6);
N-(biotine-C6)QRFSR-COOH (SEQ ID NO: 7);
NH2-dRdSdFdRdQ-COOH (retroinversion D-enantiomere) (SEQ ID NO: 8);
NH2-YQRFSR-COOH (SEQ ID NO: 9);
NH2-Y—(C6-polyethylene)QRFSR-COOH (SEQ ID NO: 10);
NH2-Y—(C12-polyethylene)QRFSR-COOH (SEQ ID NO: 11);
NH2-QRF[S—O—C8-polyethylene]R—COOH (SEQ ID NO: 12);
NH2-CQRFSR-COOH (SEQ ID NO: 13);
NH2-CQRF[S—O—C8-polyethylene]R—COOH (SEQ ID NO: 14);
NH2-CQRF[S—O—C12-polyethylene]R—COOH (SEQ ID NO: 15);
NH2-C—(C8-polyethylene)QRFSR-COOH (SEQ ID NO: 16);
NH2-C—(C12-polyethylene)QRFSR-COOH (SEQ ID NO: 17);
NH2-C—(C8-polyethylene)QRF[S—O—C8-polyethylene]R—COOH (SEQ ID NO: 18);
NH2-[Cβ2]QRF[S—O—C8-polyethylene]R—COOH (SEQ ID NO: 19);
NH2-C—(C8-polyethylene)QRFS[β3R]—COOH (SEQ ID NO: 20);
NH2-C[dQ]RF[S—O—C8-polyethylene][dR]—COOH (SEQ ID NO: 21);
NH2-C—(C8-polyethylene)QRFS[dR] (SEQ ID NO: 22);
NH2-[dC]QRF[S—O—C8-polyethylene][dR]—COOH (SEQ ID NO: 23);
NH2-[Cβ2]QRF[S—O—C8-polyethylene][β3R]—COOH (SEQ ID NO: 24);
[CQRFSR]2 (SEQ ID NO: 25) as cystine-dipeptide through disulfide linkage;
Glp-RFSR—COOH (SEQ ID NO: 26);
NH2-QRYSR-COOH (SEQ ID NO: 27);
NH2-QRF[4F]SR—COOH (SEQ ID NO: 28), wherein —F[4F]— is a phenylalanine, the phenyl group of which is substituted in the para position by a fluoro atom so that —F[4F]— has the following formula:

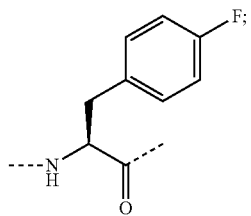

NH2-QKFSR-COOH (SEQ ID NO: 30);
NH2-QRFSK-COOH (SEQ ID NO: 31);
NH2-C—(C6-polyethylene)QRFSR-COOH (SEQ ID NO: 32);
NH2-C—(C6-polyethylene)-QRFS[S—O—C8-polyethylene]R—COOH (SEQ ID NO: 33);
NH2-C—(C12-polyethylene)QRFS[S—O—C8-polyethylene]R—COOH (SEQ ID NO: 34);
NH2-C[PE12]QRFS-dR—COOH (SEQ ID NO: 35);
NH2-C—(C12-polyethylene)-QRFS[S—O—C8-polyethylene]-β3R—COOH (SEQ ID NO: 36);
NH2-C—(C8-polyethylene)-QRFS[S—O—C8-polyethylene]-β3R—COOH (SEQ ID NO: 37), wherein
Cβ2 replaces natural Cysteine residue by β2-cysteine incorporating methylene residue adjacent to Cα carbon near the α carbonyl group of Cysteine (H$_2$N(—CH$_2$—SH)—CH$_2$—CO—);
β3R replaces natural Arginine residue by β3-Arginine incorporating methylene residue adjacent to Cα carbon near the α amine group of Arginine (—NH—CH$_2$—C[—(CH$_2$)$_3$—NH—C(NH)(NH$_2$)]—COOH);
[S—O—C8-polyethylene] and [S—O-octanoyl] mean a serine, the hydroxyl group of which is substituted by an octanoyl group;
[S—O—C12-polyethylene] means a serine, the hydroxyl group of which is substituted by a dodecanoyl group;
C6, C8 or C12—polyethylene correspond to spacer of 6, 8 or 12 ethylene carbons ((—HN—(CH$_2$)$_6$—CO—, —HN—(CH$_2$)$_8$—CO— and (—HN—(CH$_2$)$_{12}$—CO—, respectively).

In the above peptides, NH2- represents the terminal amine of the peptide and COOH the terminal carboxylic acid (—CO—NH2 when the terminal function is an amide). The list above can also be read as:
QRFSR-NH2 (SEQ ID NO: 2);
QRGPR (SEQ ID NO: 3);
QHNPR (SEQ ID NO: 4);
(Acetyl)QRFSR (SEQ ID NO: 5);
—(—HN—(CH$_2$)$_8$—CO-)-QRFSR (SEQ ID NO: 6);
biotine-(-HN—(CH$_2$)$_6$—CO-)-QRFSR (SEQ ID NO: 7);
dR-dS-dF-dR-dQ (SEQ ID NO: 8);
YQRFSR (SEQ ID NO: 9);
Y—(—HN—(CH$_2$)$_6$CO-)-QRFSR (SEQ ID NO: 10);
Y—(—HN—(CH$_2$)$_{12}$—CO-)-QRFSR (SEQ ID NO: 11);
QRF—S(O-octanoyl)-R (SEQ ID NO: 12);
CQRFSR (SEQ ID NO: 13);
CQRF—S(O-octanoyl)-R (SEQ ID NO: 14);
CQRF—S(O-dodecanoyl)-R (SEQ ID NO: 15);
C—(—HN—(CH$_2$)$_8$—CO-)-QRFSR (SEQ ID NO: 16);
C—(—HN—(CH$_2$)$_{12}$—CO-)-QRFSR (SEQ ID NO: 17);
C—(—HN—(CH$_2$)$_8$—CO-)-QRF—S(O-octanoyl)-R (SEQ ID NO: 18);
[Cβ2]QRF—S(O-octanoyl)-R (SEQ ID NO: 19);
C—(—HN—(CH$_2$)$_8$—CO-)-QRFS-[β3R] (SEQ ID NO: 20);
C-[dQ]-RF—S(O-octanoyl)-[dR] (SEQ ID NO: 21);

C—(—HN—(CH$_2$)$_8$—CO-)-QRFS-[dR] (SEQ ID NO: 22);
[dC]-QRF—S(O-octanoyl)-[dR] (SEQ ID NO: 23);
[Cβ2]-QRF—S(O-octanoyl)-[β3R] (SEQ ID NO: 24);
[CQRFSR]$_2$ (SEQ ID NO: 25);
Glp-RFSR (SEQ ID NO: 26);
QRYSR (SEQ ID NO: 27);
QR—F[4F]—SR (SEQ ID NO: 28), wherein —F[4F]— is a phenylalanine, the phenyl group of which is substituted in the para position by a fluoro atom;
QR—F[4Br]-SR (SEQ ID NO: 29), wherein —F[4Br]— is a phenylalanine, the phenyl group of which is substituted in the para position by a bromo atom;
QKFSR (SEQ ID NO: 30);
QRFSK (SEQ ID NO: 31);
C—(—HN—(CH$_2$)$_6$—CO-)-QRFSR (SEQ ID NO: 32);
C—(—HN—(CH$_2$)$_6$—CO-)-QRF—S(O-octanoyl)-R (SEQ ID NO: 33);
C(—HN—(CH$_2$)$_{12}$—CO—)QRF—S(O-octanoyl)-R (SEQ ID NO: 34);
C—(—HN—(CH$_2$)$_{12}$—CO-)-QRFS-dR (SEQ ID NO: 35);
C—(—HN—(CH$_2$)$_{12}$—CO-)-QRF—S(O-octanoyl)-β3R (SEQ ID NO: 36);
C—(—HN—(CH$_2$)$_8$—CO-)-QRF—S(O-octanoyl)β3R (SEQ ID NO: 37),
wherein:
Cβ2 is H$_2$N(—CH$_2$—SH)—CH$_2$—CO—;
β3R is —NH—CH$_2$—C[—(CH$_2$)$_3$—NH—C(NH)(NH2)]-COOH;
—S(—O-octanoyl) means a serine, the hydroxyl group of which is substituted by an octanoyl group;
—S(—O-dodecanoyl) means a serine, the hydroxyl group of which is substituted by a dodecanoyl group. The following definitions are used throughout the instant application.

A "peptide" is a molecule comprised of a linear array of amino acid residues connected to each other in the linear array by peptide bonds. Such linear array may optionally be cyclic, i.e., the ends of the linear peptide or the side chains of amino acids within the peptide may be joined, e.g., by a chemical bond. Such peptides may further include secondary, tertiary or quaternary structures, as well as intermolecular associations with other peptides or other non-peptide molecules. Such intermolecular associations may be through, without limitation, covalent binding (e.g., through disulfide linkages), or through chelation, electrostatic interactions, hydrophobic interactions, hydrogen bonding, ion-dipole interactions, dipole-dipole interactions, or any combination of the above.

Any aminoacid of the following peptides may be in L-configuration or D-configuration. In particular, the entire peptide may be either in L or D configuration. The hydrocarbon chain can optionally contain a further methylene group compared to the natural aminoacid, so that the aminoacids can also be β aminoacids, more precisely β2 or β3 aminoacids. For example, R may represent one of the following aminoacid: lR (i.e. L-Arg), dR (i.e. D-Arg), β3R or β2R. Any aminoacid of the following peptides may also be an aza-aminoacid or a β-aza-aminoacid.

"F(X)" means a phenylalanine, the phenyl group of which is substituted by one or more halogen atoms, preferably fluor, the preferred F(X) having one the following formulae:

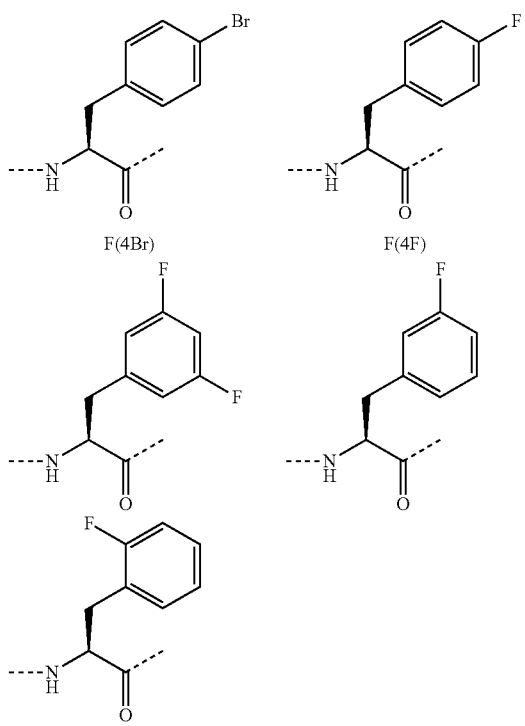

F(4Br)　　F(4F)

"S(OAlk)" means a serine, the hydroxyl group of which is substituted by a linear or branched alkyl group having from 1 to 20 carbon atoms (i.e. "Alk"), preferably an octanoyl or a dodecanoyl group. In the present application, S(O—C8-polyethylene) or S(O—C8) means a serine, the hydroxyl group of which is substituted by an octanoyl group.

"C-[linker]-" means Cys-[NH—(CH$_2$)$_n$—CO]—, wherein n is an integer between 1 and 20, preferably between 4 and 15, 6, 8 or 12 being particularly preferred. In the present application, "C—(C6-polyethylene)" or "C[PE6]" means Cys-[NH—(CH$_2$)$_6$—CO]—; "C—(C8-polyethylene)" or "C[PE8]" means Cys-[NH—(CH$_2$)$_8$—CO]—; and "C—(C12-polyethylene)" or "C[PE12]" means Cys-[NH—(CH$_2$)$_{12}$—CO]—.

"Y-[linker]-" means Tyr-[NH—(CH$_2$)$_{n'}$—CO]—, wherein n' is an integer between 1 and 20, preferably between 4 and 15, 6, 8 or 12 being particularly preferred. In the present application, "Y—(C6-polyethylene)" or "Y[PE6]" means Tyr-[NH—(CH$_2$)$_6$—CO]—; "Y—(C8-polyethylene)" or "Y[PE8]" means Tyr-[NH—(CH$_2$)$_8$—CO]—; and "Y—(C12-polyethylene)" or "Y[PE12]" means Tyr-[NH—(CH$_2$)$_{12}$—CO]—.

"Inhibitory potency" of a peptide derivative of the invention towards a particular peptidase can readily be assessed by the one skilled in the art, e.g. either by measuring Ki values or IC$_{50}$ values. In particular, where IC$_{50}$ values are determined, the relative inhibitory potencies of two modified opiorphin peptides can be compared by measuring the IC$_{50}$ value of each modified opiorphin peptide towards a given peptidase, in given experimental conditions (same buffer, same concentrations of peptidase and substrate), and by comparing said IC$_{50}$ values of the modified opiorphin peptides with the IC$_{50}$ value of opiorphin in the same experimental conditions.

The invention concerns a peptide derivative of formula (I):

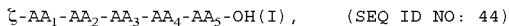

wherein:
ζ is hydrogen atom, tyrosine, Y-[linker]- or a Zn chelating group, such as cysteine, C-[linker]-, N-acetyl-cysteine, N-mercaptoacetyl (HS—CH$_2$—CO—), hydroxamic acid (HO—NH—CO—) or an optionally substituted hydroxyquinoline, AA$_1$ is Q or Glp, AA$_2$ is K, R or H, preferably R, AA$_3$ is Y, G, N, F or F(X), preferably F or F(X), AA$_4$ is P, S or S(OAlk), preferably S or S(OAlk), AA$_5$ is K or R, preferably R, C-[linker]- meaning Cys-[NH—(CH$_2$)$_n$—CO]—, wherein n is an integer between 1 and 20, n being preferably 6, 8 or 12, Y-[linker]- meaning Tyr-[NH—(CH$_2$)$_{n'}$—CO]—, wherein n' is an integer between 1 and 20, n' being preferably 6, 8 or 12, F(X) meaning a phenylalanine, the phenyl group of which is substituted by one or more halogen atoms, S(OAlk) meaning a serine, the hydroxyl group of which is substituted by a linear or branched alkyl group having from 1 to 20 carbon atoms, said AA$_1$, AA$_2$, AA$_3$, AA$_4$, and AA$_5$ may be independently either in the L-configuration or D-configuration, and any one of AA$_1$, AA$_2$, AA$_3$, AA$_4$, and AA$_5$ may be optionally a β aminoacid, an aza-aminoacid or a β-aza-aminoacid;

wherein if the peptide derivative comprises a cysteine, said peptide derivative is optionally a dimer, with the proviso that the peptide is not QRFSR (SEQ ID NO: 1), QHNPR (SEQ ID NO: 4), QRGPR (SEQ ID NO: 3), YQRFSR (SEQ ID NO: 9) or GlpRFSR (SEQ ID NO: 26).

Generally, in the peptide derivatives according to the invention, AA$_1$, AA$_2$, AA$_3$, AA$_4$, and AA$_5$ are independently either in the L-configuration or D-configuration, and any one of AA$_1$, AA$_2$, AA$_3$, AA$_4$, and AA$_5$ is optionally a β aminoacid, an aza-aminoacid or a β-aza-aminoacid.

In an embodiment, at least one of AA$_1$, AA$_2$, AA$_3$, AA$_4$, and AA$_5$ is a β aminoacid. In another embodiment, all of AA$_1$, AA$_2$, AA$_3$, AA$_4$, and AA$_5$ are β aminoacids.

In an embodiment, at least one of AA$_1$, AA$_2$, AA$_3$, AA$_4$, and AA$_5$ is an aza-aminoacid. In another embodiment, all of AA$_1$, AA$_2$, AA$_3$, AA$_4$, and AA$_5$ are an aza-aminoacids.

In an embodiment, at least one of AA$_1$, AA$_2$, AA$_3$, AA$_4$, and AA$_5$ is a β-aza-aminoacid. In another embodiment, all of AA$_1$, AA$_2$, AA$_3$, AA$_4$, and AA$_5$ are β-aza-aminoacid.

In one embodiment, the peptide derivative comprises a cysteine and is a dimer wherein two sulfur atoms of two cysteines are bound with a disulfur bond. For example, [CQRFSR]$_2$ (SEQ ID NO: 25) is the dimer of the peptide derivative CQRFSR (SEQ ID NO: 13), the cysteine aminoacids of which are linked with a disulfur bond.

In a preferred embodiment, when ζ is a hydroxyquinoline, the peptide derivative has the following formula (SEQ ID NO: 45):

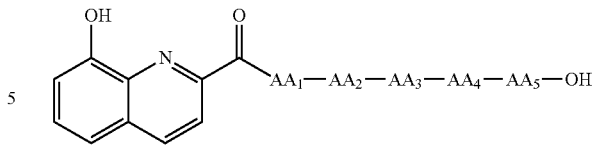

Peptide derivatives of formula (I) are modified opiorphin peptides which advantageously have inhibitory potency against neutral endopeptidase NEP and/or aminopeptidase AP-N.

Preferred peptide derivatives of formula (I) are:
CQRFSR (SEQ ID NO: 13),
QRF(X)SR (SEQ ID NO: 39),
QRGPR (SEQ ID NO: 3),
QHNPR (SEQ ID NO: 4),
QRFPR (SEQ ID NO: 38),
QRFS(OAlk)R (SEQ ID NO: 46), preferably QRFS(O-octanoyl)R (SEQ ID NO: 12),
C-[linker]-QRFSR (SEQ ID NO: 47), preferably C—[NH—(CH$_2$)$_6$—CO]-QRFSR (SEQ ID NO: 32), C—[NH—(CH$_2$)$_8$—CO]-QRFSR (SEQ ID NO: 6), or C—[NH—(CH$_2$)$_{12}$—CO]-QRFSR (SEQ ID NO: 17),
QRYSR (SEQ ID NO: 27),
QKFSR (SEQ ID NO: 30),
QRFSK (SEQ ID NO: 31),
C-[linker]-QRFSR (SEQ ID NO: 47), preferably C—[NH—(CH$_2$)$_6$—CO]-QRFSR (SEQ ID NO: 32), C—[NH—(CH$_2$)$_8$—CO]-QRFSR (SEQ ID NO: 6), or C—[NH—(CH$_2$)$_{12}$—CO]-QRFSR (SEQ ID NO: 17),
[CQRFSR]$_2$ (SEQ ID NO: 25),
C—[NH—(CH$_2$)$_6$—CO]-QRFS(OAlk)R (SEQ ID NO: 48), preferably C—[NH—(CH$_2$)$_6$—CO]-QRFS(O-octanoyl)R (SEQ ID NO: 33) and
Y—[NH—(CH$_2$)$_{12}$—CO]-QRFSR (SEQ ID NO: 11).

In an embodiment, the invention is related to a peptide derivative of formula (II):

ζ$^a$-Q-AA$^a_2$-AA$^a_3$-P-R-OH (II), (SEQ ID NO: 49)

wherein:
ζ$^a$ is a hydrogen atom or a Zn chelating group, such as cysteine, C-[linker]-, N-acetyl-cysteine, N-mercaptoacetyl (HS—CH$_2$—CO—), hydroxamic acid (HO—NH—CO—) or an optionally substituted hydroxyquinoline, AA$^a_2$ is R or H, preferably R, AA$^a_3$ is G, N, F or F(X), preferably F, said Q, AA$_2$, AA$_3$, P, and R may be independently either in the L-configuration or D-configuration, and any one of Q, AA$_2$, AA$_3$, P, and R may be optionally a β aminoacid, an aza-aminoacid or a β-aza-aminoacid;

wherein if the peptide derivative comprises a cysteine, said peptide derivative is optionally a dimer, with the proviso that the peptide is not QHNPR (SEQ ID NO: 4) or QRGPR (SEQ ID NO: 3).

Said peptide derivative of formula (II) is a modified opiorphin peptide and is advantageously a human AP-N inhibitor. In particular it may have an inhibitory potency towards AP-N higher (preferably at least 6 fold, 8 fold, or 10 fold) than its inhibitory potency towards NEP endopeptidase and/or carboxydipeptidase activity(ies).

Preferred peptide derivatives of formula (II) are:
QRGPR (SEQ ID NO: 3),
QHNPR (SEQ ID NO: 4), and
QRFPR (SEQ ID NO: 38).

In an embodiment, the invention is related to a peptide derivative of formula (III):

$$\zeta''\text{-}AA_1\text{-}AA''_2\text{-}AA''_3\text{-}AA''_4\text{-}AA''_5\text{-}OH\,(III), \quad (\text{SEQ ID NO: 50})$$

wherein:
- $\zeta''$ is a hydrogen atom, tyrosine or Y-[linker]-,
- $AA_1$ is Q or Glp, preferably Q,
- $AA''_2$ is K or R, preferably R,
- $AA''_3$ is Y, F or F(X), preferably F or F(X),
- $AA''_4$ is S or S(OAlk),
- $AA''_5$ is K or R, preferably R,
- said $AA_1$, $AA_2$, $AA_3$, $AA_4$, and $AA_5$ may be independently either in the L-configuration or D-configuration, and any one of $AA_1$, $AA_2$, $AA_3$, $AA_4$, and $AA_5$ may be optionally a β aminoacid, an aza-aminoacid or a β-aza-aminoacid;

with the proviso that the peptide is not QRFSR (SEQ ID NO: 1), QHNPR (SEQ ID NO: 4), YQRFSR (SEQ ID NO: 9) or GlpRFSR (SEQ ID NO: 26).

Said peptide derivative of formula (III) is a modified opiorphin peptide and is advantageously a human NEP inhibitor. In particular, it may have an inhibitory potency towards NEP endopeptidase and/or carboxydipeptidase activity(ies) higher (preferably at least 6 fold, 8 fold, or 10 fold than its inhibitory potency towards AP-N.

In one embodiment, the invention is related to a peptide derivative of formula (IIIa):

$$AA_1\text{-}R\text{-}AA''_3\text{-}S(OAlk)\text{-}AA''_5\text{-}OH\,(IIIa), \quad (\text{SEQ ID NO: 51})$$

wherein:
- $AA_1$ is Q or Glp,
- $AA''_3$ is F or F(X),
- $AA''_5$ is K or R, preferably R, with the proviso that the peptide is not QRFSR (SEQ ID NO: 1), QHNPR (SEQ ID NO: 4), YQRFSR (SEQ ID NO: 9) or GlpRFSR (SEQ ID NO: 26).

Preferred peptide derivatives of formula (III) or (IIIa) are:
QRYSR (SEQ ID NO: 27),
QRF(X)SR (SEQ ID NO: 39),
QKFSR (SEQ ID NO: 30),
QRFSK (SEQ ID NO: 31),
QRFS(OAlk)R (SEQ ID NO: 46), preferably QRFS(O-octanoyl)R (SEQ ID NO: 12) and Y—[NH—(CH$_2$)$_{12}$—CO]-QRFSR (SEQ ID NO: 11).

In an embodiment, the invention is related to a peptide derivative of formula (IV):

$$\zeta'''\text{-}Q\text{-}R\text{-}AA'''_3\text{-}AA'''_4\text{-}R\text{-}OH\,(IV), \quad (\text{SEQ ID NO: 52})$$

wherein:
- $\zeta'''$ is a hydrogen atom, or a Zn chelating group, such as cysteine, C-[linker]-, N-acetyl-cysteine, N-mercaptoacetyl (HS—CH$_2$—CO—), hydroxamic acid (HO—NH—CO—) or an optionally substituted hydroxyquinoline,
- $AA'''_3$ is F or F(X), preferably F(X),
- $AA'''_4$ is S or S(OAlk), preferably S or S(OAlk),
- said Q, R, AA$_3$, AA$_4$, and R may be independently either in the L-configuration or D-configuration, and any one of Q, R, AA$_3$, AA$_4$, and R may be optionally a β aminoacid, an aza-aminoacid or a β-aza-aminoacid;

wherein if the peptide derivative comprises a cysteine, said peptide derivative is optionally a dimer, with the proviso that the peptide is not QRFSR (SEQ ID NO: 1) or YQRFSR (SEQ ID NO: 9).

Peptide derivatives of formula (IV) are modified opiorphin peptides which are advantageously dual human NEP and human AP-N inhibitors, as they display significative inhibitory potency towards both human NEP and human AP-N.

Preferred peptide derivatives of formula (IV) are:
CQRFSR (SEQ ID NO: 13),
[CQRFSR]$_2$ (SEQ ID NO: 25),
C—(—HN—(CH$_2$)$_{12}$—CO-)-QRFSR (SEQ ID NO: 17);
C—(—HN—(CH$_2$)$_6$—CO-)-QRFSR (SEQ ID NO: 32);
C-[linker]QRF—S(O-octanoyl)-R (SEQ ID NO: 53), preferably C—(—HN—(CH$_2$)$_6$—CO-)-QRF—S(O-octanoyl)-R (SEQ ID NO: 33), C—(—HN—(CH$_2$)$_8$—CO-)-QRF—S(O-octanoyl)-R (SEQ ID NO: 18) or C—(—HN—(CH$_2$)$_{12}$—CO-)-QRF—S(O-octanoyl)-R (SEQ ID NO: 34);
QRF(X)SR (SEQ ID NO: 39) and
QRFS(OAlk)R (SEQ ID NO: 46), preferably QRFS(O-octanoyl)R (SEQ ID NO: 12).

Preferably, the peptide derivatives of the invention here are modified opiorphin peptides and have inhibitory potency against neutral endopeptidase NEP and/or aminopeptidase AP-N. Most preferably, the modified opiorphin peptides of the invention have inhibitory potency against endopeptidase NEP and aminopeptidase AP-N.

The peptide derivatives according to the present invention may be prepared in a conventional manner by peptide synthesis in liquid or solid phase by successive couplings of the different amino acid residues to be incorporated (from the N-terminal end to the C-terminal end in liquid phase, or from the C-terminal end to the N-terminal end in solid phase) wherein the N-terminal ends and the reactive side chains are previously blocked by conventional groups.

For solid phase synthesis the technique described by Merifield may be used in particular. Alternatively, the technique described by Houbenweyl in 1974 may also be used.

The peptide derivatives according to the present invention may also be obtained using genetic engineering methods, provided they consist of natural aminoacids.

Modifications to the opiorphin peptides include chemical (e.g., containing additional chemical moieties, such as methyl, polyethylene C$_2$, C$_4$, C$_6$, C$_8$, C$_{10}$, C$_{12}$ and polyethyleneglycol thereof, and/or glycosylated forms, and peptidomimetics (e.g., a low molecular weight compound that mimics a peptide in structure and/or function (see, e.g., Abell, *Advances in Amino Acid Mimetics and Peptidomimetics*, London: JAI Press (1997); Gante, *Peptidmimetica—massgeschneiderte Enzyminhibitoren Angew. Chem.* 106: 1780-1802 (1994); and Olson et al., *J. Med. Chem.* 36: 3039-3049 (1993)).

Other modifications which may be introduced in the peptide derivatives of the invention include using unnatural amino acids, D amino acid, β$_2$ amino acid, β$_3$ amino acid, Aza amino acid or β-Aza amino acid instead of L amino acid, conformational restraints, isosteric replacement, cyclization, or other modifications. Other examples are where one or more amide bond is replaced by a non-amide bond, and/or one or more amino acid side chain is replaced by a different chemical moiety, or one or more of the N-terminus, the C-terminus or one or more side chain is protected by a protecting group, and/or double bonds and/or cyclization and/or stereospecificity is introduced into the amino acid chain to increase rigidity and/or binding affinity.

Based on the crystal structure of the binding domain of the metallo-ectopeptidase targeted by the peptide derivative of the invention, mimetics can also be obtained by means of computer-assisted drug design development (Oefner et al. J.

Mol. Biol. (2000) 296(2):341-9; Gomeni et al. Eur. J. Pharm. Sci. (2001) 13(3):261-70; Kan, Curr Top Med Chem (2002), 2(3):247-69).

Still other modifications include:
- protecting the $NH_2$ and COOH hydrophilic groups by esterification (COOH) with lipophilic alcohols or by amidation (COOH) and/or by acetylation ($NH_2$) or added carboxyalkyl or aromatic hydrophobic chain at the $NH_2$ terminus;
- retroinversion isomers of the CO—NH amide bonds or methylation (or ketomethylene, methyleneoxy, hydroxyethylene) of the amide groups;
- insertion of —[HN—$(CH_2)_n$—CO—]— moieties between two aminoacids, n being an integer from 1 to 20, preferably 6, 8 or 12.

The nucleic acids, also named polynucleotides, such as DNA or RNA molecules, that encode the peptides, including peptide derivatives containing natural amino acids, defined above are also part of the invention, while taking into account the degeneration of the genetic code. Preferably, the nucleic acid comprises a sequence incoding a peptide derivative which consists of natural aminoacids.

The nucleic acids of the invention include sequences that are hybridizable to any of the above sequences or their complementary sequences under high stringency hybridization conditions which refers to hybridization and/or washing conditions at 68° C. in 0.2×SSC, at 42° C. in 50% formamide, 4×SSC, or under conditions that afford levels of hybridization equivalent to those observed under either of these two conditions.

The present invention further relates to vectors for cloning and/or expression comprising a nucleic acid sequence of the invention and to host cell comprising the nucleic acid or said vector, i.e. a host cell wherein at least one of these vectors was transferred. The expression vector according to the invention comprises a nucleic acid sequence encoding a peptide, including a peptide derivative, or protein of the invention, said nucleic acid sequence being operably linked to elements allowing its expression. The vector advantageously contains a promoter sequence, signals for initiation and termination of translation, as well as appropriate regions for regulation of translation. Its insertion into the host cell may be transient or stable. The vector may also contain specific signals for secretion of the translated protein.

Host cells may be prokaryotic or eukaryotic, including but not limited to bacteria, yeasts, plant cells, insect cells, mammalian cells, including cell lines which are commercially available. Preferred examples for host cells are COS-1, HEK cells, 293 cells, or CHO cells.

The present invention further provides antibodies, monoclonal or polyclonal, or fragments thereof specifically directed against (i.e. that specifically recognizes) the modified opiorphin peptides described herein. Such antibodies may be useful for instance for studying pharmacokinetic properties of the peptide derivatives of the invention.

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', F(ab')2 and F(v).

Procedures for raising polyclonal antibodies are also well known. Typically, such antibodies can be raised by administering the peptide derivative, including conjugate peptide derivative, of the present invention subcutaneously to New Zealand white rabbits which have first been bled to obtain pre-immune serum. The antigens can be injected at a total volume of 50 µl per site at ten different sites or at least five different sites. The rabbits are then bled five weeks after the first injection and periodically boosted with the same antigen administered subcutaneously at five fold lower concentration than the primary injection at maximum depending on quality of the immune response three times every six weeks. A sample of serum is then collected every 10 days after each boost. Polyclonal antibodies are then recovered from the serum by affinity chromatography using the corresponding antigen to capture the antibody. This and other procedures for raising polyclonal antibodies are disclosed in E. Harlow, et. al., editors, Antibodies: A Laboratory Manual, Cold Spring Harbor Laboratory, New York (1988).

A "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g. a bispecific monoclonal antibody.

Laboratory methods for preparing monoclonal antibodies are well known in the art (see, for example, Harlow et al., supra). Monoclonal antibodies (Mabs) may be prepared by immunizing a mammal, e.g. a mouse, rat, rabbit, goat, human and the like, against the peptide derivatives of the present invention, including conjugated peptide derivatives. The antibody-producing cells in the immunized mammal are isolated and fused with myeloma or heteromyeloma cells to produce hybrid cells (hybridoma). The hybridoma cells producing the monoclonal antibodies are used as a source of the desired monoclonal antibody.

While Mabs can be produced by hybridoma culture, the invention is not to be so limited. Also contemplated is the use of Mabs produced by an expressing nucleic acid cloned from a hybridoma. That is, the nucleic acid expressing the molecules secreted by a hybridoma can be transferred into another cell line to produce a transformant. The transformant is genotypically distinct from the original hybridoma but is also capable of producing antibody molecules of this invention, including immunologically active fragments of whole antibody molecules, corresponding to those secreted by the hybridoma. In addition, the literature provides methods for forming chimeric antibodies, humanized antibodies, single chain antibodies and the like variations on a basic immunoreactive antibody fragment. All of these are considered within the scope of the invention insofar as a class and specificity of antibody is disclosed and claimed, regardless of the precise variant structure that one skilled in the art may construct.

The modified opiorphin peptides can be formulated in pharmaceutical compositions in association with a pharmaceutically acceptable carrier. For instance, the pharmaceutical compositions are suitable for a topical, oral, sublingual, parenteral, intranasal, intravenous, intramuscular, subcutaneous, transcutaneous or intraocular administration and others.

The modified opiorphin peptides described above are useful in the treatment of diseases or disorders, wherein a modulation of the activity of a membrane metallo-ectopeptidase is sought, more particularly a membrane-zinc metallopeptidase, such as NEP and AP-N.

Natural NEP substrates are mainly the peptide hormones: Enkephalins, Substance P, Bradykinin, Angiotensin II and Atrial Natriuretic Peptide which play key role in the control of central and peripheral pain perception, inflammatory phenomena, mineral exchange and/or arterial tone (Rogues et al., Pharmacol Rev. 1993; 45(1):87-146).

More particularly, neutral endopeptidase, NEP 24-11, is distributed both in nervous and peripheral tissues of mammals, and in the periphery it is particularly abundant in the kidney and placenta. In these tissues the cell-surface metallopeptidase NEP participates in the postsecretory processing and metabolism of neuropeptides, systemic immunoregulatory peptides and peptide-hormones. By controlling the active levels of circulating or secreted regulatory peptides, NEP modulates their physiological receptor-mediated action. Hence, the membrane-anchored NEP is involved in regulating the activity of: potent vasoactive peptides such as Substance P, Bradykinin (BK), Atrial Natriuretic peptide (ANP), and Angiotensin II (AII); potent inflammatory/immunoregulatory peptides such as Substance P and BK and fMet-Leu-Phe (fMLP); potent opioid neuropeptides such as Met and Leu-Enkephalins (Enk) and potent mineral exchange and fluid homeostasis regulatory peptides such as ANP, C-type Natriuretic Peptide (CNP) and B-type Natriuretic Peptide (BNP). However the levels of these peptides are changed through the NEP-induced formation/degradation only in regions where they are tonically released or where their release is triggered by a stimulus.

From an integrative point of view, the NEP biological activity is to control the active levels of peptidergic signals involved in arterial tension regulation, in inflammatory phenomena, emotional states and in water-mineral homeostasis, as well as, in the control of pain processing. From a clinical point of view, this substantiates the fact that NEP is an important drug target in various disease states. For example, by inhibiting NEP and APN, thereby increasing the levels and duration of action of central or peripheral endogenous opioids, an analgesic effect or an anti-depressant or psychostimulant effect could be obtained. The main advantage of modifying the concentrations of endogenous regulatory peptides by use of NEP and/or AP-N inhibitors is that the pharmacological effects are induced only at receptor sites activated by the natural ligands, and are critically dependent on their tonic or stimulus-evoked release happening upon specific environmental, behavioral and physiopathological stressful situations (Rogues et al, 1993).

Examples of mammalian membrane metallopeptidases besides NEP are NEP2, ECE (Endothelin-Converting Enzymes), in particular ECE1 and ECE2, the erythrocyte cell-surface antigen KELL and the product of PEX gene associated with X-linked hypophosphatemic rickets and AP-N (Aminopeptidase N).

NEP2 is distributed specifically in the nervous system and genital tissues.

AP-N is a ubiquitous enzyme present in a wide variety of human organs, tissues and cell types (endothelial, epithelial, fibroblast, leukocyte) and is in particular abundant in the kidneys and central nervous system. Identified substrates include Angiotensin III (Ang III); neuropeptides, including enkephalins and endorphins; and hormones, including kallidan and somatostatin. AP-N is a multifunctional enzyme, related with tumorigenesis, immune system, pain, regulation of arterial blood pressure etc. AP-N is also involved in the trimming of antigen and the process of antigen presentation. These functions facilitate the modulation of bioactive peptide responses (pain management, vasopressin release) and influence immune functions and major biological events (cell proliferation, secretion, invasion, angiogenesis) thereby providing treatment options for many kinds of diseases.

Inhibition of ECE has a significant application in the treatment of hypertension and the prevention and treatment of atherosclerosis.

Inhibition of AP-N in conjunction with NEP has significant application in the treatment of pain and depression, anxiety, sedation and socio-sexual emotional disorders.

Inhibition of related membrane metallopeptidases has therapeutic effects in the treatment of tumors, namely ovarian, colorectal, brain, lung, pancreas, gastric and melanoma cancers, and reducing the incidence of metastasis, atherosclerosis and/or hypertension.

Inhibition of related membrane metallopeptidases has effects in pain relief. Such antinociceptive effects on acute pain are analgesic effects but also effects on chronic inflammatory pain such as arthritis or inflammatory bowel disease, post-operative injury and neuropathic severe pain associated or not with cancer and/or cancer therapy.

Furthermore, inhibition of bacterial or viral metallopeptidase is expected to have anti-infection effects.

Metallopeptidases playing an important role in pathogen host tissue invasion and immunological and inflammatory processes, for example those of *Streptococcus pyogenes*, *Pseudomonas aeruginosa*, *Porphyromonas gingivalis* and *Legionella pneumophila*.

Furthermore, bacterial metallopeptidases, especially zinc-metallopeptidases play an important role in the diseases caused by proteolytic toxins, such as the toxins of *B. anthracis* (Anthrax Lethal factor) and the neurotoxins of *C. tetanum* and *botulinum*.

Other metallopeptidases play an important role in various infections such as infections caused by HIV (FR 2 707 169).

The importance of proteinase inhibitors for the treatment of bacterial or viral diseases may be found in J. Potempa and J. Travis.

The different roles of metallopeptidases are disclosed in Turner et al, 2001; Kenny et al, 1977; Kenny et al, 1987; Beaumont et al, 1996.

One object of the present invention is providing an analgesia or anti-depressant therapy with the modified opiorphin peptides which acts by inhibiting NEP and AP-N at peripheral, spinal and/or supraspinal levels and thereby increasing the levels and duration of action of central or peripheral endogenous opioids, including enkephalins.

The treatment of pain, especially acute and chronic pain, visceral inflammatory and neuropathic pain, is contemplated.

The treatment of any hydro-mineral imbalance is also an aim of the invention. Among target disorders one may cite bone, teeth, kidney, parathyroid, pancreas, intestine, stomach mucosa, prostate, and salivary gland disorders that are caused by hydro-mineral imbalance.

In particular, the disorder may be selected from hyper or hypo-parathyroidism, osteoporosis, pancreatitis, submandibular gland lithiasis, nephrolithiasis and osteodystrophy.

The treatment of impaired interpersonal and behavioural disorders is of further interest. Various mental disorders are described in WO 02/051434.

In particular the invention is drawn at any disorder selected from the group consisting of avoidance disorder, decreased awareness disorder, autistic disorder, attention deficit hyperactivity disorder, arousal disorder, hospitalism, impaired interpersonal functioning and relationship to the external world, schizoid personality disorder, schizophrenia, depressive disorder, decreased interest in environment, impaired social activity linked to sexuality, and impaired sexual behaviour, including untimely ejaculation, hyperactive sexuality and erectile dysfunction.

The invention also relates to the use of the peptides or peptide derivatives according to the invention as psychostimulating agents. Accordingly the prevention or treatment of a narcolepsy, hypersomnia, obsessional compulsive troubles, mood disorders such as depressive disorders or major depressive disorder, either major depressive disorder single episode or major depressive disorder recurrent, type I or II bipolar disorder, dysthymic disorder and cyclothymic disorder.

Diseases wherein a modulation of a membrane metallopeptidase is sought also include hypertension, aterosclerosis, tumor, inflammatory arthritis and bowel disease.

Treatment of infections is also encompassed. Especially, the importance of proteinase inhibitors for the treatment of bacterial or viral diseases may be found in J. Potempa and Travis.

The modified opiorphin peptides described above are also useful for controlling immuno-inflammatory responses.

The modified opiorphin peptides as defined above are also useful as a natriuretic agent or a diuretic agent.

Thus, the present invention advantageously provides peptide derivatives as defined above for use in the treatment of a disease or disorder selected from the group consisting of pain, depressive disorders, impaired social activity linked to sexuality, and impaired sexual behaviour.

Another object of the present invention is the use of the above described peptide derivatives or nucleic acids as a substitute in the treatment of drug abuse, notably morphine drug abuse.

Indeed, studies have suggested that the vulnerability to drug abuse and the development of reward and drug dependence is at least in part, a result of pre-existent or induced modifications and/or defect of the endogenous opioid system. In this regard, using modified opiorphin peptides or nucleic acid to potentiate the effects of endogenous enkephalins will reduce the various side-effects (somatic signs of withdrawal) produced by interruption of chronic morphine or heroin administration.

Preferred diseases or disorders which may be treated with the peptide derivatives of the invention include pain, depressive disorders, impaired social activity linked to sexuality, and impaired sexual behaviour.

The invention further relates to the use of an agent that modulates the interaction between endogenous BPLP protein or maturation product, e.g. natural opiorphin QRFSR (SEQ ID NO: 1), and a membrane metallopeptidase for the preparation of a therapeutic composition for preventing or treating diseases wherein a modulation of the activity of said membrane metallopeptidase is sought.

The invention provides an in vitro method for screening compounds for their ability to bind to the NEP and/or APN binding site for the BPLP protein or a the QRFSR (SEQ ID NO: 1) peptide. Details of this procedure are described, e.g., in U.S. application Ser. No. 10/593,071 filed on Sep. 15, 2006, also published as WO 2005/090386, as well as in the international patent application PCT/EP2009/050567, the contents of which are incorporated herein by reference.

Another object of the present invention is a process for determining the relative affinity of the modified opiorphin peptides that specifically bind to the NEP and/or to the AP-N binding sites for the BPLP protein, or maturation products, (or the peptide that retains the binding specificity or the physiological activity of the BPLP protein or of its matured products) as described in e.g., in U.S. application Ser. No. 10/593, 071 filed on Sep. 15, 2006, the contents of which are incorporated herein by reference.

EXAMPLES

Example 1

Methods for Biochemical Assays

Formal kinetic analysis was performed for each assay using real-time fluorescence monitoring of specific substrate hydrolysis. For each 96-well adapted fluorimetric model, all parameters allowing the analysis of human NEP and human AP-N enzyme activity were defined under conditions of initial velocity measurement.

1—Sources of the Human Ectopeptidases, hNEP and hAP-N

Recombinant human NEP and recombinant human AP-N (devoid of their respective N-terminal cytosol and transmembrane segment) that were purchased from R&D Systems, were used as pure source of peptidase.

2—Substrates and Synthetic Inhibitors

In vitro, Amino-, CarboxyDi- and Endo-Peptidase activities were assayed by measuring the breakdown of the following synthetic selective substrates:

Abz-dR-G-L-EDDnp (SEQ ID NO: 42) FRET-peptide that is an internally quenched fluorescent substrate specific for NEP-EndoPeptidase activity, was synthesized by Thermo-Fisher Scientific (Germany).

Abz-R-G-F-K-DnpOH (SEQ ID NO: 40) FRET-peptide that is an internally quenched fluorescent substrate specific for NEP-CarboxyDiPeptidase activity, was synthesized by Thermo-Fisher Scientific (Germany)

Mca-R-P-P-G-F-S-A-F-K-(Dnp)-OH (SEQ ID NO: 41) FRET-peptide (Mca-BK2) that is an intramolecularly quenched fluorogenic peptide structurally related to bradykinin, which is a selective substrate for measuring NEP and ECE activity, was purchased from R&D Systems.

FRET is the distance-dependant transfer of energy from a donor fluorophore (Abz=ortho-aminobenzoyl or Mca=7-methoxycoumarin-4-yl-acetyl) to an acceptor fluorophore (DnpOH=2,4-dinitrophenyl or EDDnp=2,4-dinitrophenyl ethylenediamine).

L-alanine-Mca, Ala-Mca, a fluorogenic substrate for measuring aminopeptidase activity was purchased from Sigma.

Measuring the hydrolysis rate of these substrates by soluble ectopeptidases in the presence and absence of different available selective synthetic peptidase inhibitors assessed the specificity of each enzyme assay:—Thiorphan (NEP inhibitor) (Bachem),—Bestatin (AP inhibitor) (Calbiochem).

3—Measurement of Peptidase Activities Using 96-Well Adapted Fluorimetric Assays

According to conditions of initial velocity measurement: the time, pH and temperature of incubation as well as enzyme and substrate concentrations were defined for each assay. Hydrolysis of substrates was measured by real-time monitoring their metabolism rate by the two peptidases in the presence and absence of tested inhibitory compound (concentrations ranging from 1 to 50 µM). These were added to the preincubation medium. The background rate of substrate autolysis representing the fluorescent signal obtained in the absence of enzyme was subtracted to calculate the initial velocities in RFU (Relative Fluorescent Unit)/min.

Measurement of NEP-endopeptidase activity using FRET specific peptide-substrate, Abz-dR-G-L-EDDnp (SEQ ID NO: 42). Using black half-area 96 well microplate, the standard reaction consisted of enzyme (12.5 ng) in 100 mM Tris-HCl pH 7 containing 200 mM NaCl (100 µl final volume). The substrate (15 µM final concentration) was added after preincubation for 10 min at 28° C. and the kinetics of appearance of the fluorescent signal (RFU) was directly analyzed for 40 min at 28° C. (2.3 min-interval successive measures) by using a fluorimeter microplate reader (monochromator Infinite 200-Tecan) at 320 nm and 420 nm excitation and emission wavelengths, respectively.

Under conditions of initial velocity measurement, the intensity of the signal was directly proportional to the quantity of metabolites formed during the 20-40 min time-period of the reaction. Thus, in absence of inhibitor, the initial velocity of rhNEP-mediated specific endoproteolysis of Abz-dR-G-L-EDDnp (SEQ ID NO: 42), was calculated from the linear regression (slope–NEP activity in presence of vehicle/incubation time) as 8218±2878 RFU/min/µg rhNEP, n=3 independent determinations.

Measurement of NEP-CarboxyDiPeptidase activity using FRET specific peptide-substrate Abz-R-G-F-K-DnpOH (SEQ ID NO: 40). Using black half-area 96 well microplate, the standard reaction consisted of enzyme (2.5 ng) in 100 mM Tris-HCl pH 6.5 containing 50 mM NaCl (100 µl final volume). The substrate (4 µM final concentration) was added after preincubation for 10 min and the kinetics of appearance of the fluorescent signal (RFU) was directly analyzed for 40 min at 28° C. (2.3 min-interval successive measures) by using the fluorimeter reader at 320 nm excitation and 420 nm emission wavelengths. Under these conditions of initial velocity measurement, human NEP-mediated specific hydrolysis of Abz-R-G-F-K-DnpOH (SEQ ID NO: 40) was evaluated at 59796±18685 RFU/min/µg rhNEP, n=4 independent determinations. NEP-CarboxyDiPeptidase activity assayed with the substrate Abz-R-G-F-K-DnpOH (SEQ ID NO: 40) is referred to as "NEP-CDP1 activity" in FIGS. 5-8.

In addition, the intramolecularly quenched fluorogenic peptide, Mca-BK2 (10 µM), was submitted to hydrolysis by 5 ng rhNEP under the same experimental conditions as those described behind. Under these conditions the hNEP-enzyme acted upon Mca-R-P-P-G-F-S-A-F-K-(Dnp)-OH (SEQ ID NO: 41) mainly as a CarboxyDiPeptidase preferentially cleaving A-F bond but also as an EndoPeptidase cleaving the G-F bond. Under conditions of initial velocity measurement, human NEP-mediated specific hydrolysis of Mca-BK2 was evaluated at 121910±24755 RFU/min/µg rhNEP, n=3 independent determinations. NEP-CarboxyDiPeptidase activity assayed with the substrate Abz-R-G-F-K-DnpOH (SEQ ID NO: 40) is referred to as "NEP-CDP2 activity" in FIGS. 5-8.

Measurement of AP-N-ectopeptidase activity using Ala-Mca substrate. Using black half-area 96 well microplate the standard reaction consisted of enzyme (4 ng) in 100 mM Tris-HCl pH 7.0 (100 µl final volume). The Ala-Mca substrate (25 µM final concentration) was added after preincubation for 10 min at 28° C. and the kinetics of appearance of the signal was monitored for 40 min at 28° C. by using the fluorimeter reader at 380 nm excitation and 460 nm emission wavelengths. The intensity of the signal was directly proportional to the quantity of metabolites formed during the 10-40 min time-period of the reaction. Under these conditions of initial velocity measurement, the human AP-N-mediated aminoproteolysis of Ala-Mca was directly calculated (from the slope: AP-N activity in absence of inhibitor in function of incubation time) as 147042±44657 RFU/min/µg rhAP-N, n=3 independent determinations.

Other FRET-peptide substrates for assaying NEP carboxydipeptidase activity have been described in Barros et al. Biol. Chem., 2007, 388:447-455.

Example 2

Results of Biochemical Assays

1—Screening of Opiorphin Peptide-Derivatives on hNEP and hAP-N

Compounds were tested in triplicate at 50 µM final concentration.

FIGS. 1 to 9 display the results of biochemical assays on NEP endopeptidase and carboxydipeptidase activities and AP-N activity with various peptide derivatives of the invention.

Various Opiorphin peptido-analogs were tested for their inhibitory potency towards the two membrane-anchored ectoenzymes, NEP (specific endopeptidase and carboxydipeptidase activities) and APN by using selective fluorescence-based enzyme assays: the FRET-based Enzyme in Vitro Models previously developed and validated in the laboratory (PCT application PCT/filed Jan. 18, 2009, incorporated herein by reference).

The following compounds were analyzed. In the compounds below, NH2-represents the terminal amine of the peptide and COOH the terminal carboxylic acid of the peptide.

NH2-QRFSR-CONH2 (Opiorphin) (SEQ ID NO: 2);
  NH2-QRGPR-COOH (SEQ ID NO: 3); NH2-QHNPR-COOH (SEQ ID NO: 4);
NH2-QR(4BromoF)SR—COOH (i.e. QRF(4Br)SR); NH2-QRFPR-COOH (SEQ ID NO: 29): they displayed inhibitory preference for human AP-N and a weak inhibitory potency towards human NEP
  N-(Acetyl)QRFSR-COOH (SEQ ID NO: 5); N—(C8-polyethylene)QRFSR-COOH (SEQ ID NO: 6);
N-(biotine-C6-polyethylene)QRFSR-COOH (SEQ ID NO: 7): they displayed weak inhibitory potency towards human AP-N and NEP with a preference for NEP endopeptidase activity
  NH2-dRdSdFdRdQ-COOH (retroinversion D-enantiomere) (SEQ ID NO: 8): It did not display significant inhibitory activity towards human AP-N and NEP with a preference for AP-N activity
  NH2-YQRFSR-COOH (SEQ ID NO: 9); NH2-Y—(C6-polyethylene)QRFSR-COOH (SEQ ID NO: 10);
NH2-Y—(C12-polyethylene)QRFSR-COOH (SEQ ID NO: 11): they displayed inhibitory preference for human NEP endopeptidase activity in particular Y—(C12-polyethylene)QRFSR (SEQ ID NO: 11)
  NH2-QRF[S—O—C8-polyethylene]R—COOH (SEQ ID NO: 12); NH2-CQRFSR-COOH (SEQ ID NO: 13): They were potent dual inhibitors of human NEP (specific endopeptidase and carboxydipeptidase activities) and AP-N.
  Other modified opiorphin peptides are:
  NH2-CQRF[S—O—C8-polyethylene]R—COOH (SEQ ID NO: 14);
  NH2-CQRF[S—O—C12-polyethylene]R—COOH (SEQ ID NO: 15)
  NH2-C—(C8-polyethylene)QRFSR-COOH (SEQ ID NO: 16);
  NH2-C—(C12-polyethylene)QRFSR-COOH (SEQ ID NO: 17)
  NH2-C—(C8-polyethylene)QRF[S—O—C8-polyethylene]R—COOH (SEQ ID NO: 18)

NH2-[Cβ2]QRF[S—O—C8-polyethylene]R—COOH (SEQ ID NO: 19)

NH2-C—(C8-polyethylene)QRFS[β3R]—COOH (SEQ ID NO: 20)

NH2-C[dQ]RF[S—O—C8-polyethylene][dR]—COOH (SEQ ID NO: 21)

NH2-C—(C8-polyethylene)QRFS[dR] (SEQ ID NO: 22)

NH2-[dC]QRF[S—O—C8-polyethylene][dR]—COOH (SEQ ID NO: 23)

NH2-[Cβ2]QRF[S—O—C8-polyethylene][β3R]—COOH (SEQ ID NO: 24)

[CQRFSR]2 (SEQ ID NO: 25) as cystine-dipeptide through disulfide linkage.

Figure 9:
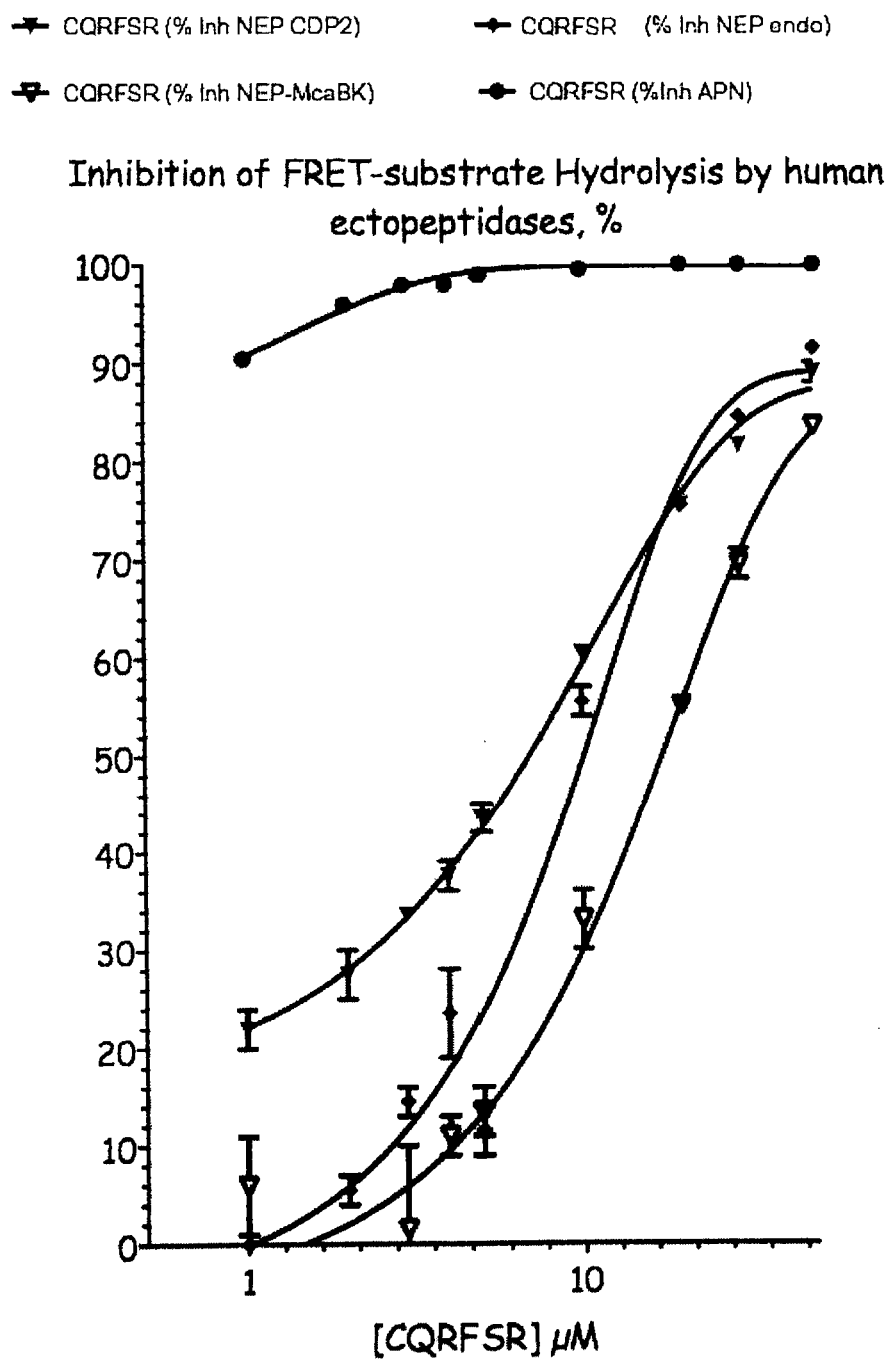
FIG. 9: Concentration-dependent Inhibition by CQRFSR peptide (SEQ ID NO: 13) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of CQRFSR-peptide (SEQ ID NO: 13) plotted in µM (log-scale).
Figure 18:
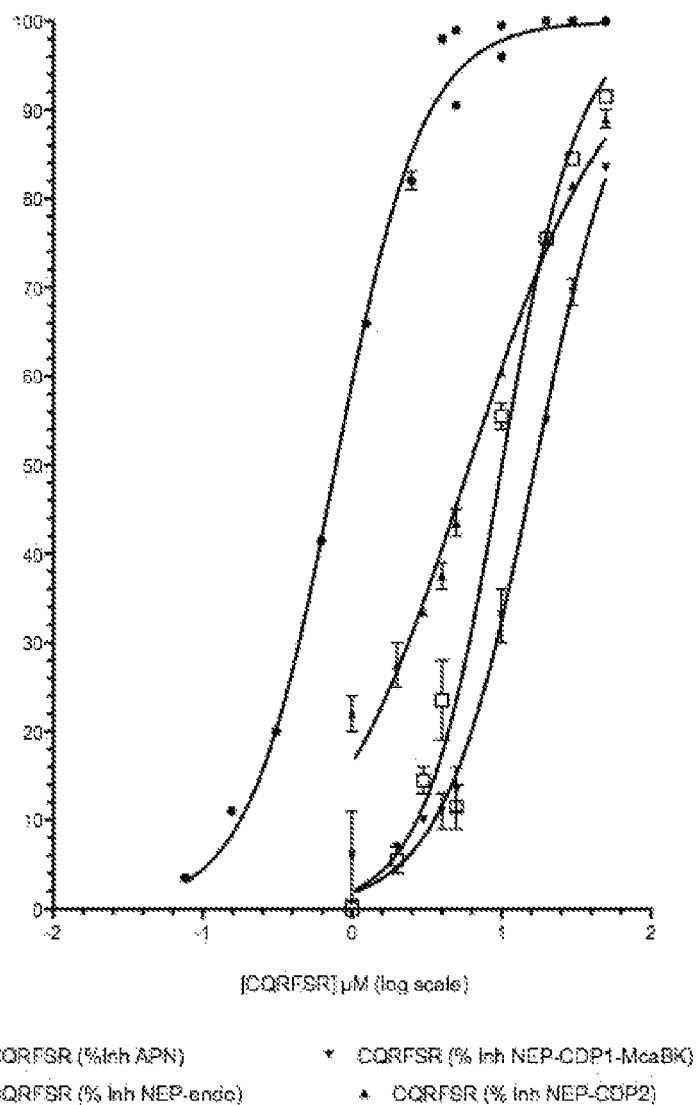
FIG. 18: Concentration-dependent Inhibition by CQRFSR peptide (SEQ ID NO: 13) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of CQRFSR-peptide (SEQ ID NO: 13) plotted in µM (log-scale).

2—Concentration-Dependent Inhibition of Selected Opiorphin Peptide-Derivatives on hNEP and hAP-N CQRFSR-COOH (SEQ ID NO: 13) peptide (FIGS. 9 and 18)

The CQRFSR-COOH (SEQ ID NO: 13) peptide prevented in a concentration dependent manner the Abz-dR-G-L-EDDnp (SEQ ID NO: 42) cleavage mediated by the rhNEP-Endopeptidase activity: $r^2=0.97$, n=18 determination points, with a IC50 at 7±3 µM.

CQRFSR-COOH (SEQ ID NO: 13) peptide prevented in a concentration dependent manner the Abz-R-G-F-K-DnpOH (SEQ ID NO: 40) cleavage mediated by the rhNEP activity: $r^2=0.99$, n=18 determination points, with a IC50 at 6±1 µM.

CQRFSR-COOH (SEQ ID NO: 13) peptide prevented in a concentration dependent manner the Ala-AMC cleavage mediated by the rhAP-N activity: $r^2=0.99$, n=30 determination points, with a IC50 at 0.8±0.1 µM.

CQRFSR-COOH (SEQ ID NO: 13) peptide prevented in a concentration dependent manner the Mca-R-P-P-G-F-S-A-F-K-(Dnp)-OH (SEQ ID NO: 41) FRET-peptide (Mca-BK2) cleavage mediated by the rhNEP activity: $r^2=0.99$, n=16 determination points, with a IC50 at 17±2 µM.

Therefore, modification of the N-terminal position of the NH2-QRFSR (SEQ ID NO: 1) peptide by formation of amide link with a Cysteine amino acid (the thiol functional group is a strong Zn-chelating group) led to a compound (CQRFSR (SEQ ID NO: 13) peptide) displaying reinforced inhibitory potency towards hAP-N (10-fold compared to QRFSR (SEQ ID NO: 1) native peptide) and towards hNEP (5-fold).

Figure 10:
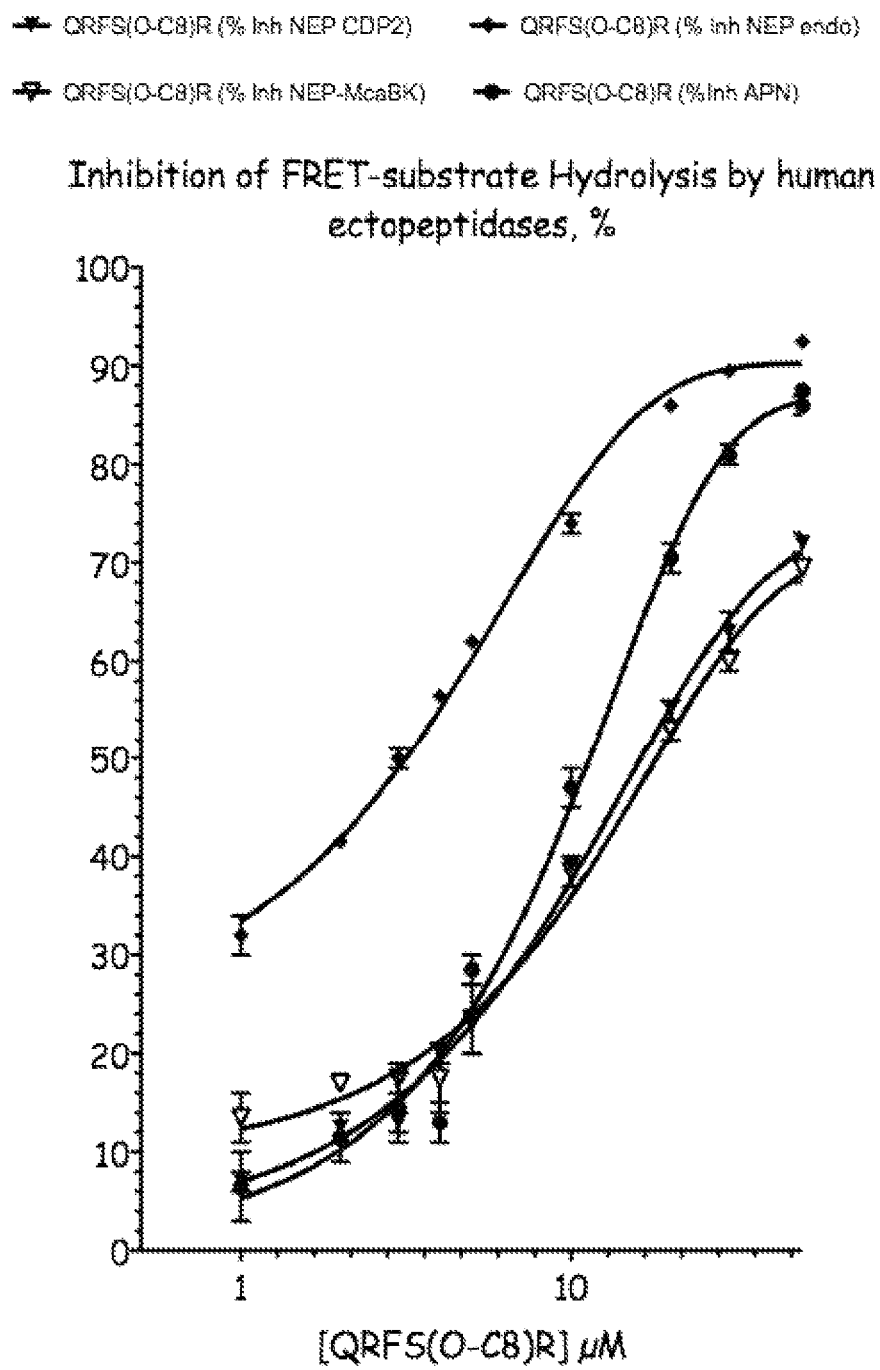
FIG. 10: Concentration-dependent Inhibition by QRFS[O-octanoyl]R peptide (SEQ ID NO: 12) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of QRFS[O-octanoyl]R-peptide (SEQ ID NO: 12) plotted in µM (log-scale).

QRF[S—O-Octanoyl]R (SEQ ID NO: 12) peptide (FIG. 10)

QRF[S—O—C8]R (SEQ ID NO: 12) peptide prevented in a concentration dependent manner the Abz-dR-G-L-EDDnp (SEQ ID NO: 42) cleavage mediated by the rhNEP-Endopeptidase activity: $r^2=0.98$, n=18 determination points, with a IC50 at 2.8±0.2 µM.

QRF[S—O—C8]R (SEQ ID NO: 12) peptide prevented in a concentration dependent manner the Abz-R-G-F-K-DnpOH (SEQ ID NO: 40) cleavage mediated by the rhNEP activity: $r^2=0.99$, n=18 determination points, with a IC50 at 12±5 µM.

QRF[S—O—C8]R (SEQ ID NO: 12) peptide prevented in a concentration dependent manner the Ala-AMC cleavage mediated by the rhAP-N activity: $r^2=0.99$, n=20 determination points, with a IC50 at 10±1 µM.

QRF[S—O—C8]R (SEQ ID NO: 12) peptide prevented in a concentration dependent manner the Mca-R-P-G-F-S-A-F-K-(Dnp)-OH (SEQ ID NO: 41) FRET-peptide (Mca-BK2) cleavage mediated by the rhNEP activity: $r^2=0.99$, n=18 determination points, with a IC50 at 14±4 µM.

Figure 11:
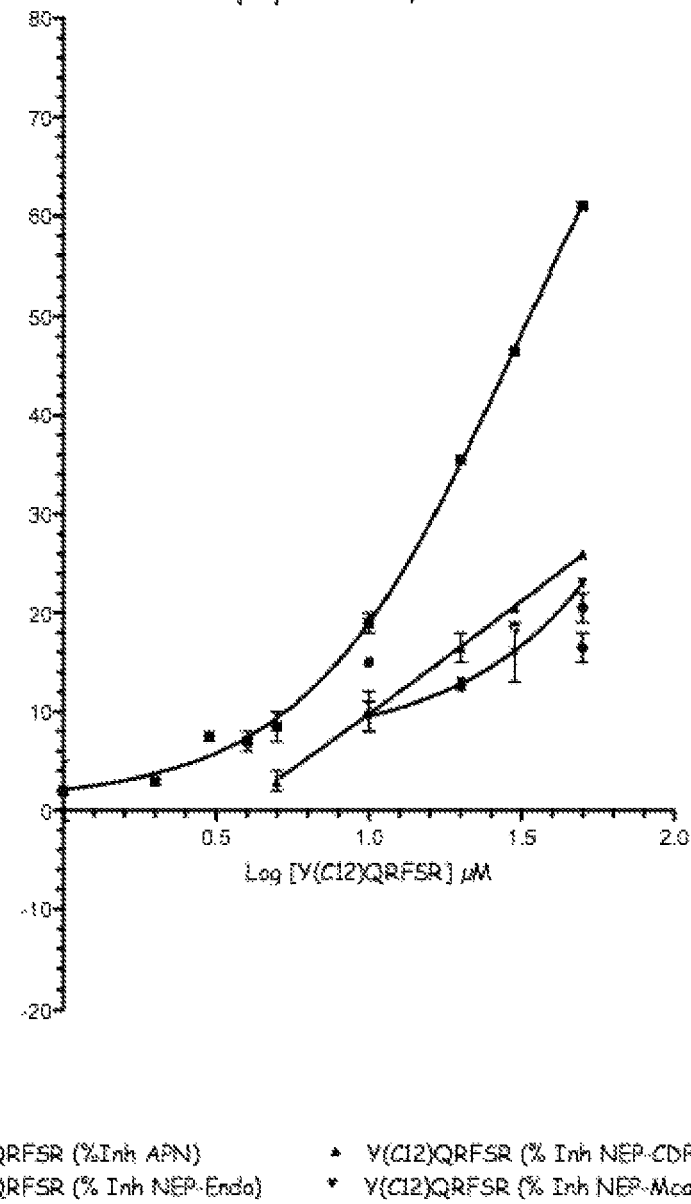
FIG. 11: Concentration-dependent Inhibition by Y(PE12)QRFSR (i.e. Y—[NH—(CH$_2$)$_{12}$—CO]-QRFSR) peptide (SEQ ID NO: 11) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of Y(PE12)QRFSR-peptide (SEQ ID NO: 11) plotted in Log µM.
Figure 13:
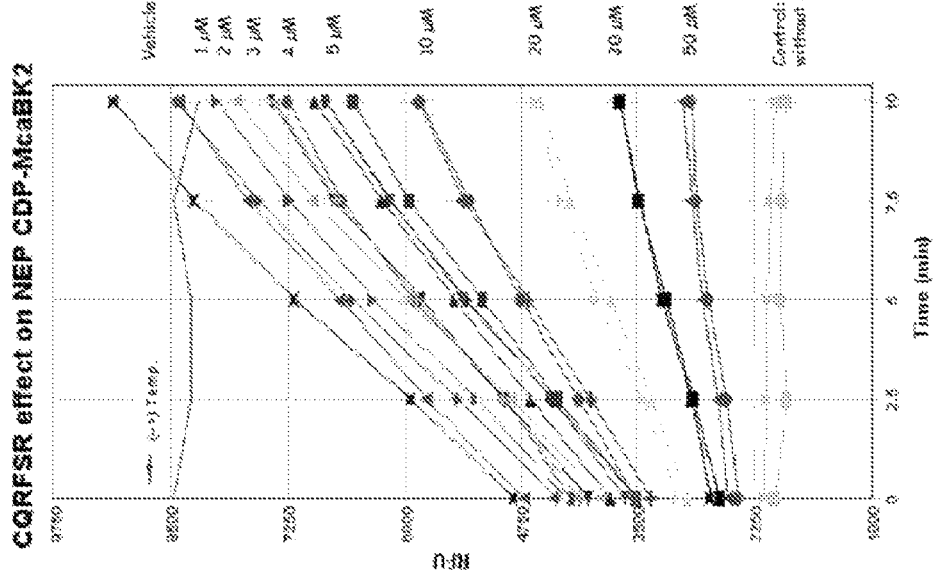
FIGS. 12-17: Kinetics of hydrolysis of corresponding FRET-peptide substrates by recombinant hNEP or hAP-N in the presence of vehicle or in the presence of 1 to 50 µM of CQRFSR (SEQ ID NO: 13) or CQRFS[O-octanoyl]R Opiorphin-peptide (SEQ ID NO: 14) analogs. Each point represents the intensity of the signal expressed in RFU (Relative Fluorescence Unit), which was proportional to the quantity of metabolites formed, as function of reaction time (min).
Figure 12:
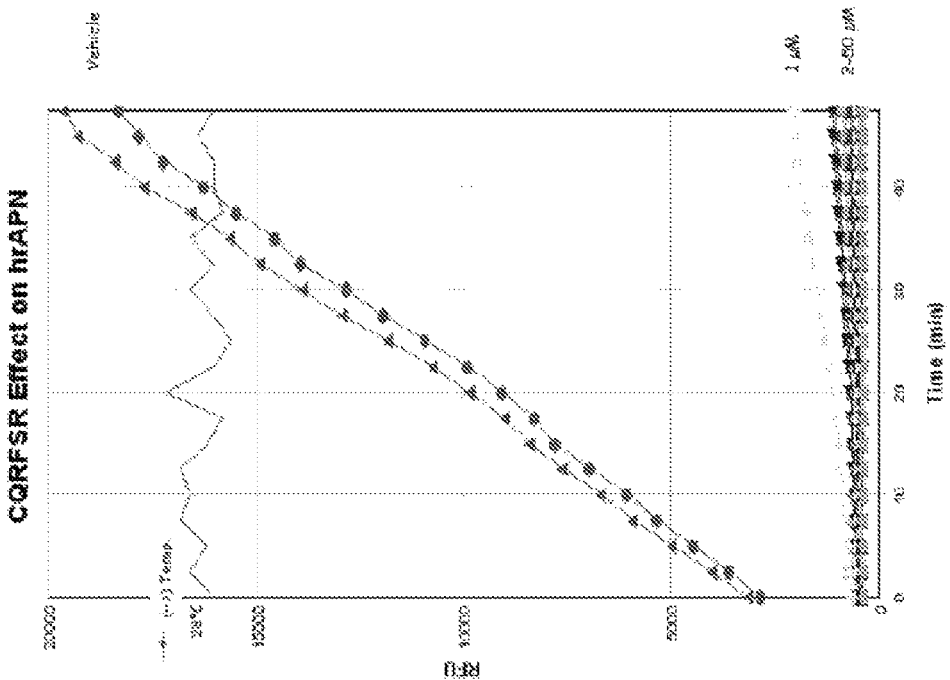
Figures 14, 15:
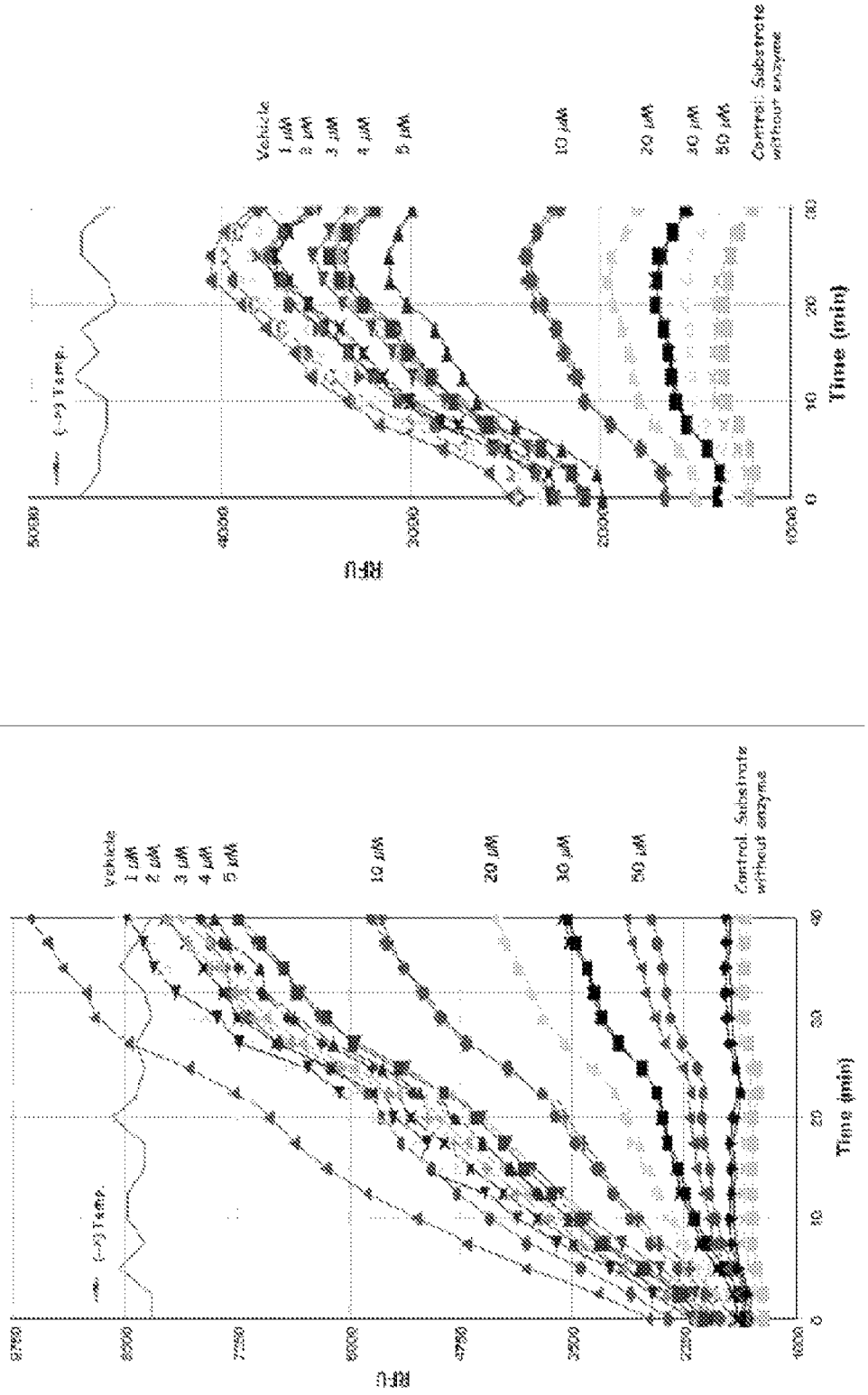
Figures 16, 17:
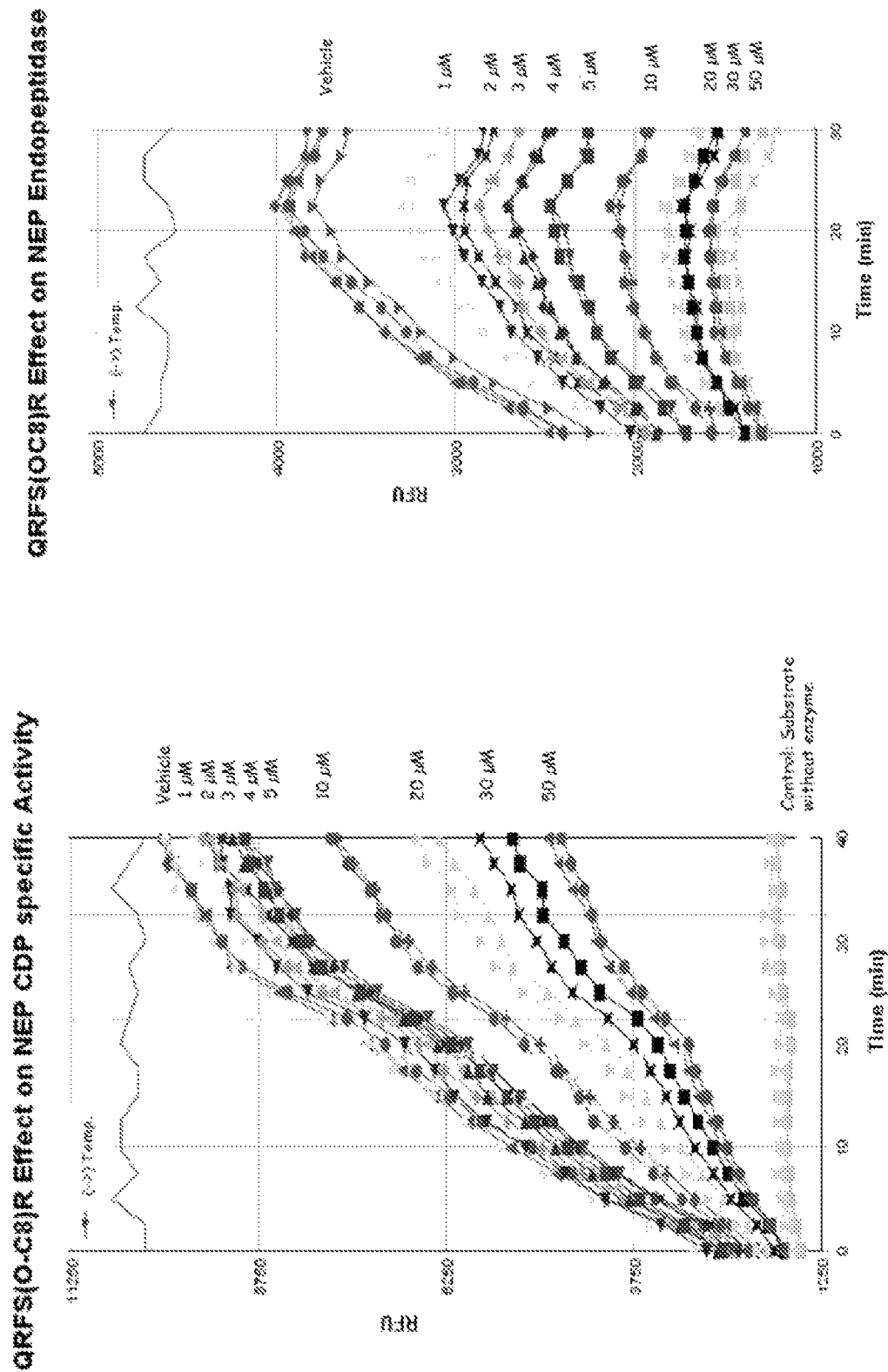
Figure 19:
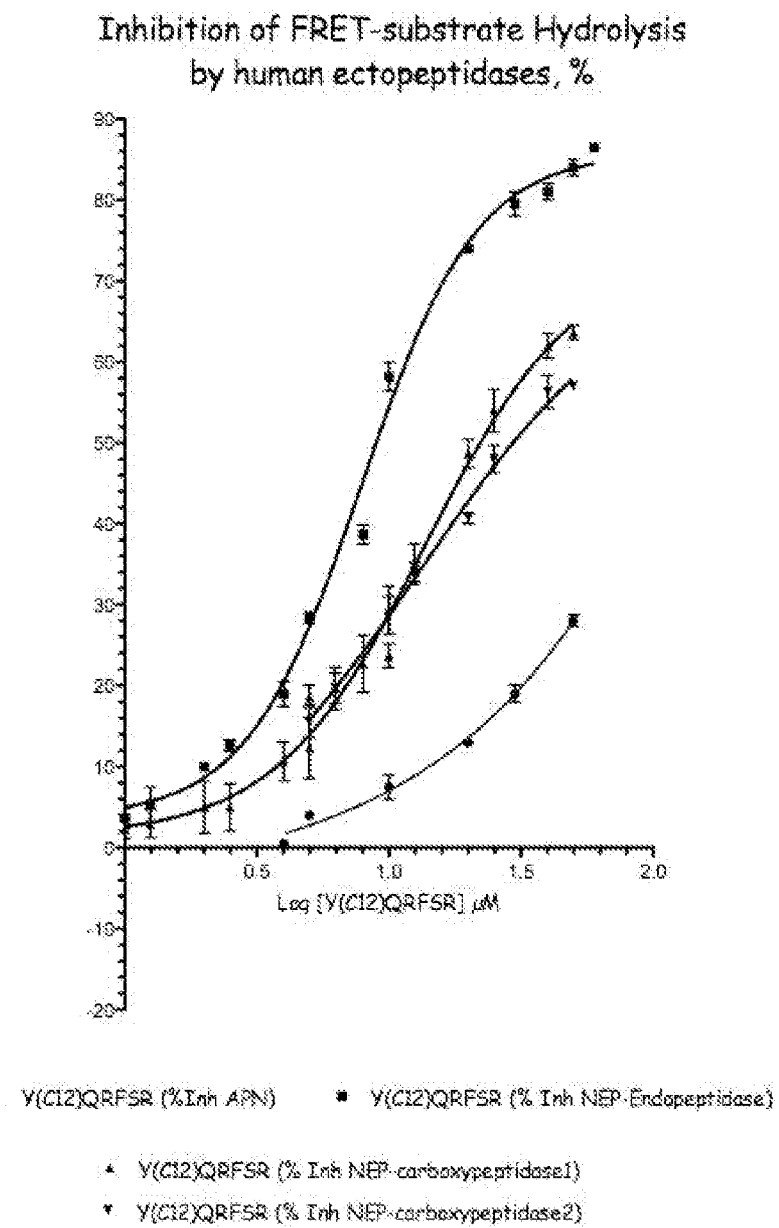
FIG. 19: Concentration-dependent Inhibition by Y[PE12]QRFSR-COOH peptide (i.e. Y—(—HN—(CH$_2$)$_{12}$—CO-)-QRFSR) (SEQ ID NO: 11) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of Y(PE12)QRFSR-COOH (SEQ ID NO: 11) peptide plotted in µM (log scale).

Y-[amino-dodecanoic-acid spacer]-QRFSR (SEQ ID NO: 11) peptide (FIGS. 11 and 19)

Y(PE12)QRFSR-COOH (SEQ ID NO: 11) peptide prevented in a concentration dependent manner the Abz-dR-G-L-EDDnp (SEQ ID NO: 42) cleavage mediated by the rhNEP-Endopeptidase activity: $r^2=0.98$, n=18 determination points, with a IC50 at 10±1 µM.

Y(PE12)QRFSR-COOH (SEQ ID NO: 11) peptide prevented in a concentration dependent manner the Abz-R-G-F-K-DnpOH (SEQ ID NO: 40) cleavage mediated by the rhNEP activity: $r^2=0.99$, n=18 determination points, with a IC50 at 24±2 µM.

Y(PE12)QRFSR-COOH (SEQ ID NO: 11) peptide prevented in a concentration dependent manner the Ala-AMC cleavage mediated by the rhAP-N activity: $r^2=0.99$, n=20 determination points, with a IC50 at 122±20 µM.

Figure 20:
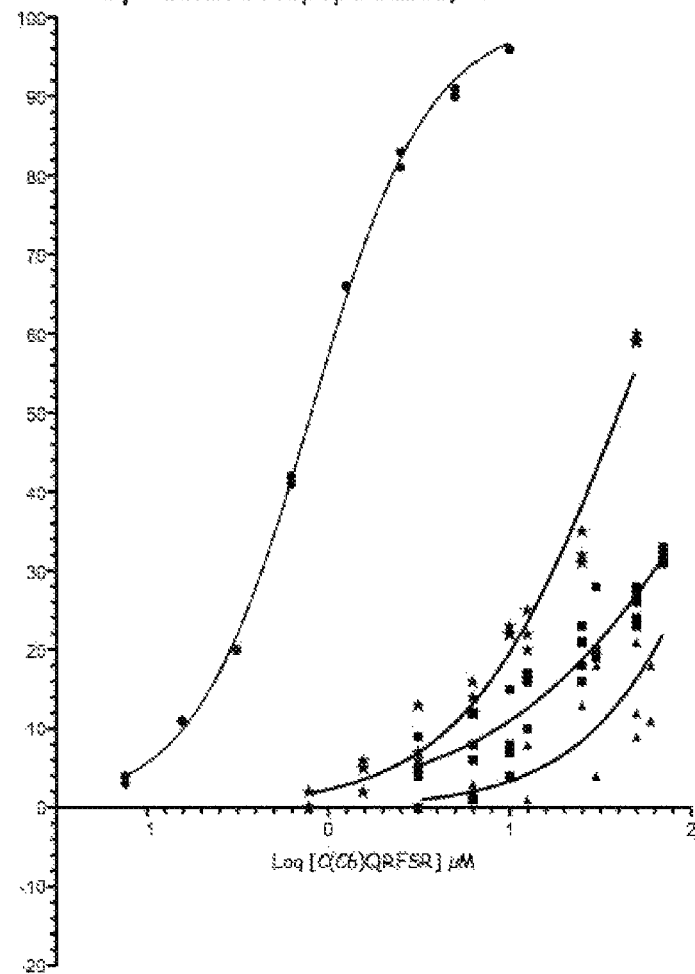
FIG. 20: Concentration-dependent Inhibition by C[PE6]QRFSR-COOH peptide (i.e. C—(—HN—(CH$_2$)$_6$—CO-)-QRFSR) (SEQ ID NO: 32) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of C[PE6]QRFSR-COOH (SEQ ID NO: 32) peptide plotted in µM (log scale).

Y(PE12)QRFSR-COOH (SEQ ID NO: 11) peptide prevented in a concentration dependent manner the Mca-R-P-G-F-S-A-F-K-(Dnp)-OH (SEQ ID NO: 41) FRET-peptide (Mca-BK2) cleavage mediated by the rhNEP activity: $r^2=0.99$, n=18 determination points, with a IC50 at 31±2 µM. Thus the inhibitory preference for human NEP endopeptidase activity of Y—(C12-polyethylene)QRFSR (SEQ ID NO: 11) was confirmed C[PE6]QRFSR (SEQ ID NO: 32) peptide (PE6=amino-hexanoic-acid) (FIG. 20)

C[PE6]QRFSR-COOH (SEQ ID NO: 32) peptide prevented in a concentration dependent manner the Abz-dR-G-L-EDDnp (SEQ ID NO: 42) cleavage mediated by the rhNEP-Endopeptidase activity: $r^2=0.98$, n=18 determination points, with a IC50 at 40±5 µM.

C[PE6]QRFSR-COOH (SEQ ID NO: 32) peptide prevented in a concentration dependent manner the Abz-R-G-F-K-DnpOH (SEQ ID NO: 40) cleavage mediated by the rhNEP activity: $r^2=0.99$, n=18 determination points, with a IC50 at about 217.

C[PE6]QRFSR-COOH (SEQ ID NO: 32) peptide prevented in a concentration dependent manner the Ala-AMC cleavage mediated by the rhAP-N activity: $r^2=0.99$, n=20 determination points with a IC50 at 0.8±0.1 µM.

C[PE6]QRFSR-COOH (SEQ ID NO: 32) peptide prevented in a concentration dependent manner the Mca-R-P-G-F-S-A-F-K-(Dnp)-OH (SEQ ID NO: 41) FRET-peptide (Mca-BK2) cleavage mediated by the rhNEP activity: $r^2=0.99$, n=18 determination points, with a IC50 at about 227 µM.

Figure 21:
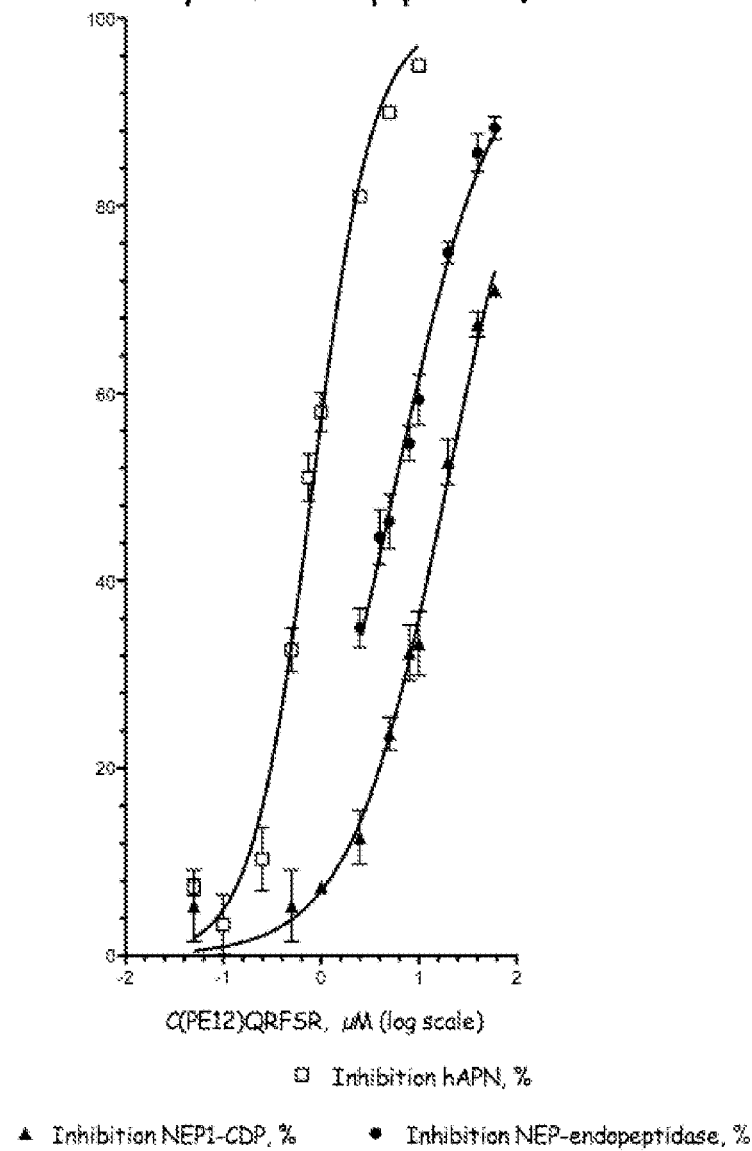
FIG. 21: Concentration-dependent Inhibition by C(PE12)QRFSR-COOH peptide (i.e. C—(—HN—(CH$_2$)$_{12}$—CO-)-QRFSR) (SEQ ID NO: 17) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of C(PE12)QRFSR-COOH (SEQ ID NO: 17) peptide plotted in µM (log scale).

C-[amino-dodecanoic-acid-spacer]-QRFSR (SEQ ID NO: 17) peptide (FIG. 21)

C[PE12]QRFSR-COOH (SEQ ID NO: 17) peptide prevented in a concentration dependent manner the Abz-dR-G-L-EDDnp (SEQ ID NO: 42) cleavage mediated by the rhNEP-Endopeptidase activity: $r^2=0.96$, n=24 determination points, with a IC50 at 5.7±0.5 µM.

C[PE12]QRFSR-COOH (SEQ ID NO: 17) peptide prevented in a concentration dependent manner the Abz-R-G-F-K-DnpOH (SEQ ID NO: 40) cleavage mediated by the rhNEP activity: $r^2=0.97$, n=30 determination points, with a IC50 at 19±2 µM.

C[PE12]QRFSR-COOH (SEQ ID NO: 17) peptide prevented in a concentration dependent manner the Ala-AMC cleavage mediated by the rhAP-N activity: $r^2=0.98$, n=27 determination points, with a IC50 at 0.8±0.1 µM.

Figure 22:
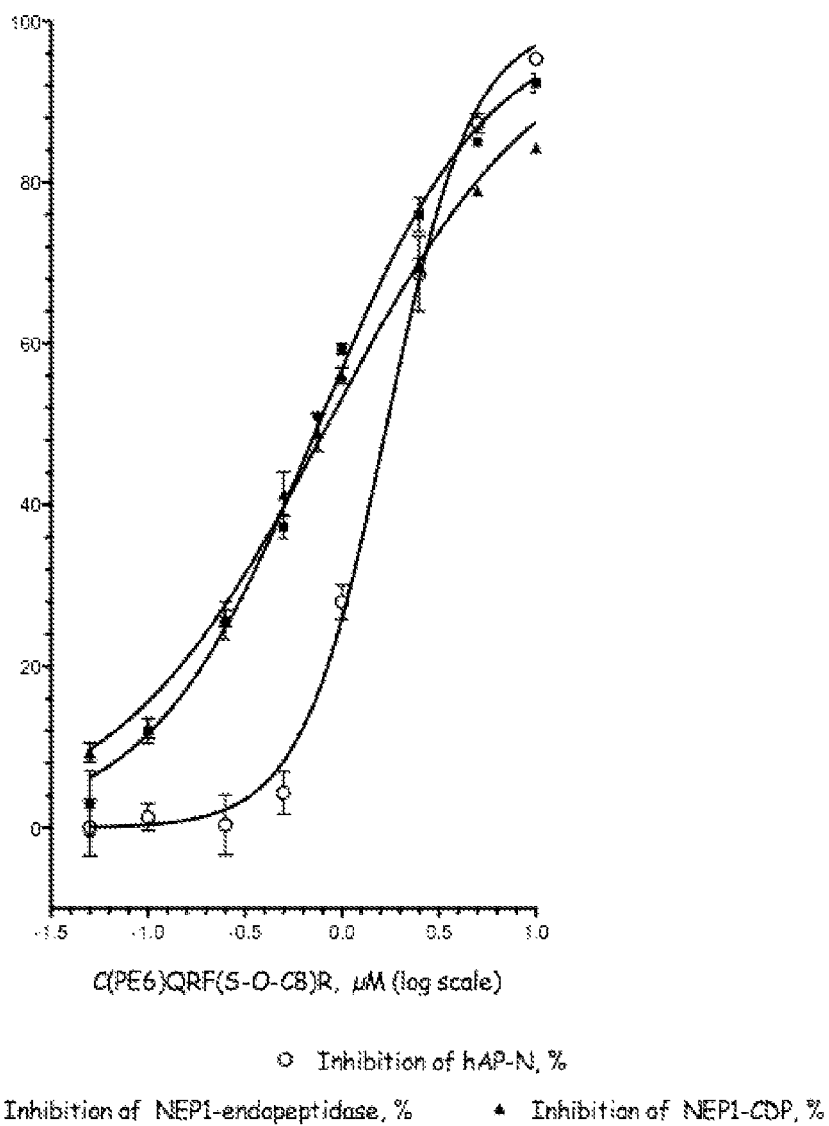
FIG. 22: Concentration-dependent Inhibition by C[PE6]QRF[S—O-Octanoyl]R peptide (i.e. C—(—HN—(CH$_2$)$_6$—CO-)-QRF—S(O-octanoyl)-R) (SEQ ID NO: 33) of hydrolysis of corresponding FRET-peptide substrates by pure recombinant human hNEP or AP-N. Each point represents the percentage of intact substrate recovered and calculated as: percentage of velocity without inhibitor—velocity in presence of inhibitor/velocity without inhibitor, which was measured in the absence or in the presence of various concentrations of C[PE6]QRF[S—O-Octanoyl]R-peptide (SEQ ID NO: 33) plotted in µM (log scale).

C-[amino-hexanoic-acid spacer]-QRFS[O-Octanoyl]R (SEQ ID NO: 33) peptide (FIG. 22)

C[PE6]QRF[S—O-Octanoyl]R (SEQ ID NO: 33) peptide prevented in a concentration dependent manner the Abz-dR-G-L-EDDnp (SEQ ID NO: 42) cleavage mediated by the rhNEP-Endopeptidase activity: $r^2=0.99$, n=27 determination points, with a IC50 at 759±56 nM.

C[PE6]QRF[S—O-Octanoyl]R (SEQ ID NO: 33) peptide prevented in a concentration dependent manner the Abz-R-G-F-K-DnpOH (SEQ ID NO: 40) cleavage mediated by the rhNEP activity: $r^2=0.99$, n=27 determination points, with a IC50 at 848±58 nM.

C[PE6]QRF[S—O-Octanoyl]R (SEQ ID NO: 33) peptide prevented in a concentration dependent manner the Ala-AMC cleavage mediated by the rhAP-N activity: $r^2=0.99$, n=24 determination points, with a IC50 at 1.7±0.1 µM.

Figure 23:
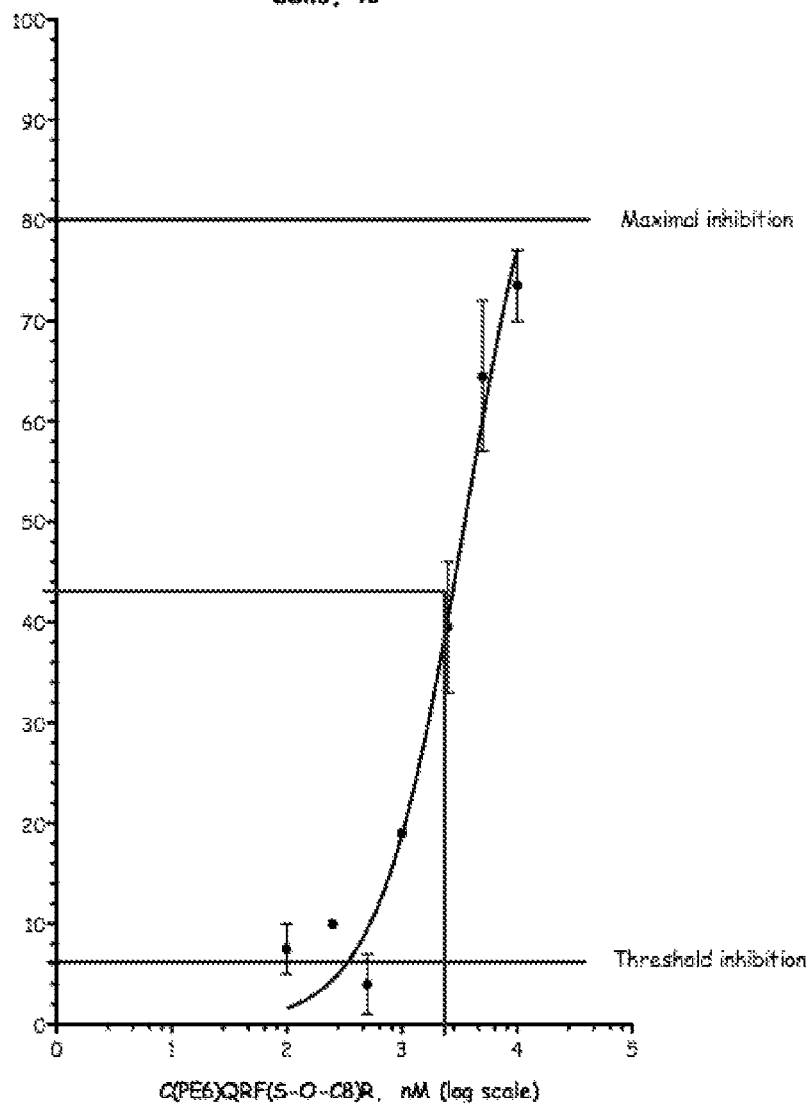
FIG. 23: Concentration-dependent Inhibition by C[PE6]QRF[S—O-Octanoyl]R peptide (i.e. C—(—HN—(CH$_2$)$_6$—CO-)-QRF—S(O-octanoyl)-R) (SEQ ID NO: 33) of hydrolysis of the substance P physiological NEP-substrate by membrane-bound human NEP expressed by LNCaP epithelial cells in culture. Each point represents the percentage of intact substrate recovered and calculated as: percentage of velocity without inhibitor—velocity in presence of inhibitor/velocity without inhibitor, which was measured in the absence or in the presence of various concentrations of C[PE6]QRF[S—O-Octanoyl]R-peptide (SEQ ID NO: 33) plotted in nM (log scale).

In a biologically relevant in vitro assay, using the Substance P physiological NEP-substrate and human cell membranes as source of hNEP, the C[PE6]QRF[S—O-Octanoyl]R (SEQ ID NO: 33) derivative peptide prevented in a concentration dependent manner the Substance P cleavage mediated by the membrane-bound hNEP-Endopeptidase activity: r2=0.95, n=13 determination points, with a IC50 at 1.6±0.4 µM (at least 5-fold increase inhibitory potency compared to Opiorphin native peptide for the same test) (FIG. 23).

[CQRFSR] dipeptide ([CQRFSR]$_2$) (SEQ ID NO: 25)

[CQRFSR] dipeptide (SEQ ID NO: 25) prevented in a concentration dependent manner the Abz-dR-G-L-EDDnp (SEQ ID NO: 42) cleavage mediated by the rhNEP-Endopeptidase activity: $r^2=0.87$, n=24 determination points, with a IC50 at 1.4±0.5 µM.

[CQRFSR] dipeptide (SEQ ID NO: 25) prevented in a concentration dependent manner the Abz-R-G-F-K-DnpOH (SEQ ID NO: 40) cleavage mediated by the rhNEP activity: $r^2=0.99$, n=27 determination points, with a IC50 at 3.3±0.2 µM.

[CQRFSR] dipeptide (SEQ ID NO: 25) prevented in a concentration dependent manner the Ala-AMC cleavage mediated by the rhAP-N activity: $r^2=0.99$, n=24 determination points, with a IC50 at 0.8±0.1 µM.

TABLE 1

Summary of IC50 values of various peptides and peptide derivatives on NEP and AP-N activities

| Opiorphin derivatives | IC50, µM towards hAP-N | IC50, µM towards hNEP-Endopeptidase | IC50, µM towards hNEP-CarboxyDiPeptidase |
|---|---|---|---|
| Y-[PE12]QRFSR (SEQ ID NO: 11) | 122 ± 20 | 10 ± 1 | 24 ± 2/31 ± 2 |
| QRFS[O-C8]R (SEQ ID NO: 12) | 10 ± 1 | 2.8 ± 0.2 | 12 ± 5/14 ± 4 |
| CQRFSR (SEQ ID NO: 13) | 0.8 ± 0.1 | 7 ± 3 | 6 ± 1/17 ± 2 |
| C-[PE6]-QRFSR (SEQ ID NO: 32) | 0.8 ± 0.1 | 40 ± 5 | ~220 |
| C-[PE12]-QRFSR (SEQ ID NO: 17) | 0.8 ± 0.1 | 5.7 ± 0.5 | 19 ± 2 |
| C-[PE6]-QRFS[O-C8]R (SEQ ID NO: 33) | 1.7 ± 0.1 | 0.76 ± 0.06 | 0.85 ± 0.06 |
| [CQRFSR]2 (SEQ ID NO: 25) | 0.8 ± 0.1 | 1.4 ± 0.5 | 3.3 ± 0.2 |

All together data showed the importance of the N-terminal α amine-group of the NH2-QRFSR (SEQ ID NO: 1) peptide for the inhibitory potency of Opiorphin towards human AP-N.

Indeed, as compared to Opiorphin-QRFSR (SEQ ID NO: 1) native peptide, its acetylation (Ac-QRFSR) (SEQ ID NO: 5) or cyclisation (pGlu-RFSR) (SEQ ID NO: 26), its octanoylation (C8-QRFSR) (SEQ ID NO: 6) or biotinylation (biotine-C6)QRFSR (SEQ ID NO: 7), led to compounds displaying a weak inhibitory potency towards hAP-N.

However, compared to Opiorphin-QRFSR (SEQ ID NO: 1) native peptide, the two compounds: pGlu-RFSR (SEQ ID NO: 26) and C8-QRFSR (SEQ ID NO: 6) displayed at least equivalent if not better inhibitory potency for human hNEP.

These data further demonstrate the importance of the free carboxyl terminus of the QRFSR-COOH (SEQ ID NO: 1) peptide for its inhibitory potency towards hNEP, especially towards the CarboxyDiPeptidase activity of NEP as compared to Opiorphin (QRFSR) (SEQ ID NO: 1) native peptide, amidation (QRFSR-CONH2) (SEQ ID NO: 2) led to a compound displaying a weak inhibitory potency towards hNEP activity.

The Phe residue of the QRFSR (SEQ ID NO: 1) peptide is important for the inhibitory potency of Opiorphin towards hNEP and hAP-N peptidase activities. Indeed, as compared to Opiorphin (QRFSR) (SEQ ID NO: 1) native peptide, substitution of Tyr residue for Phe (QRYSR) (SEQ ID NO: 27) led to a compound displaying a 6-fold decrease in inhibitory potency for hAP-N and a light reduction of inhibitory potency towards human NEP.

However, interestingly substitution of 4-Fluoro-Phe residue for Phe (QR[4F]FSR) (SEQ ID NO: 28) led to a compound displaying only a 2-fold decrease in inhibitory potency towards hNEP and a equivalent inhibitory potency towards hAP-N compared to Opiorphin-QRFSR (SEQ ID NO: 1) native peptide. Conversely, substitution of (4Bromo-Phe) residue or Phe (QR[4Br]FSR) (SEQ ID NO: 29) led to a compound displaying a weak inhibitory potency towards human NEP.

Modification of the RFS central residues of the QRFSR (SEQ ID NO: 1) peptide affects the inhibitory potency of Opiorphin towards hNEP, since, as compared to Opiorphin-QRFSR (SEQ ID NO: 1) native peptide, the compounds QRGPR (SEQ ID NO: 3), QHNPR (SEQ ID NO: 4), and QRFPR (SEQ ID NO: 38) displayed equivalent inhibitory potency for human AP-N and a weak inhibitory potency towards human NEP.

The results further demonstrate the importance of the guanidium ion of the Arg residue at position 2 of the QRFSR (SEQ ID NO: 1) peptide for the inhibitory potency of Opiorphin towards hAPN. As compared to Opiorphin-QRFSR (SEQ ID NO: 1) native peptide, substitution of a E-amine of Lys residue (QKFSR) (SEQ ID NO: 30) for Arg2 led to a compound displaying more than a 10-fold decrease in inhibitory potency towards hAP-N and a light reduction in inhibitory potency towards human NEP.

Similarly the guanidium ion of the Arg residue at position 5 of the QRFSR (SEQ ID NO: 1) peptide is important for the inhibitory potency of Opiorphin towards hAPN, as compared to Opiorphin-QRFSR (SEQ ID NO: 1) native peptide, substitution of a ϵ-amine of Lys residue for Arg5 (QRFSK) (SEQ ID NO: 31) led to a compound displaying a 10-fold decrease in inhibitory potency for hAP-N and an equivalent inhibitory potency for human NEP.

Interestingly, esterification of the hydroxyl group of the serine residue of the QRFSR (SEQ ID NO: 1) peptide by octanoic acid (QRF[octanoyl-Serine]R) (SEQ ID NO: 12) led to a compound displaying equivalent inhibitory potency towards hAP-N compared to Opiorphin-QRFSR native peptide and reinforced inhibitory potency towards hNEP-Endo and CarboxyDi-peptidase activities (at least 10-fold more inhibitory potency than Opiorphin native peptide) (see FIG. 19).

Example 3

Identification of In Vitro Potent Bioactive Peptido-Mimetics of Opiorphin that would Potentially Displaying In Vivo Bioavailability Properties Superior to the Native Peptide 1. Potential Gain in Biological Adsorption: Trans-Membrane Transport (Epithelial and Endo-Epithelial Cell Membrane Passage)

Modifications to Opiorphin-peptide by addition of chemical hydrophobic moieties such as polyethylene C6, C8, C10 or C12 spacers would allow to increase its biological in vivo adsorption potency towards membranes. Among all compounds tested, NH2-QRF[S—O-Octanoyl]R—COOH (SEQ ID NO: 12)—NH2-Y(PE12)QRFSR-COOH (SEQ ID NO: 11) (PE=[CH$_2$]n; PE12=amino-dodecanoic-acid) were shown to be potent dual inhibitors of human NEP (specific Endopeptidase and CarboxyDiDeptidase activities) and AP-N activities 2—Potential Gain in Metabolic Stability: Cystine-Dipeptide: [CQRFSR]$_2$ (SEQ ID NO: 25)

[CQRFR] di-peptide (SEQ ID NO: 25) displayed at least 2-fold increase inhibitory potency towards hNEP-Endo and CarboxyDi-peptidase activities compared to CQRFSR (SEQ ID NO: 13) monomer peptide. The di-peptide sequence should allow to protect the derivative compound against degradation by circulating aminopeptidase.

Obviously, numerous modifications and variations of the present invention are possible in light of the above teachings. It is therefore to be understood that within the scope of the appended claims, the invention may be practiced otherwise than as specifically described herein.

The invention claimed is:

1. A method of treatment of pain in a subject in need of such treatment, wherein, the method comprising administering to the subject a peptide derivative of formula (I):

$$\zeta\text{-}AA_1\text{-}AA_2\text{-}AA_3\text{-}AA_4\text{-}AA_5\text{-}OH, \quad (I) \text{ (SEQ ID NO: 44)}$$

wherein:

$\zeta$ is hydrogen atom, tyrosine, Y-[linker]- or a Zn chelating group, $AA_1$ is Q or Glp, $AA_2$ is K, R or H, $AA_3$ is Y, G, N, F or F(X), $AA_4$ is P, S or S(OAlk), $AA_5$ is K or R, Y-[linker]- meaning Tyr-[NH—(CH$_2$)$_{n'}$—CO]—, wherein n' is an integer between 1 and 20, F(X) meaning a phenylalanine, the phenyl group of which is substituted by one or more halogen atoms, S(OAlk) meaning a serine, the hydroxyl group of which is substituted by a linear or branched alkanoyl group having from 1 to 20 carbon atoms, said $AA_1$, $AA_2$, $AA_3$, $AA_4$, and $AA_5$ are independently either in the L-configuration or D-configuration, and any one of $AA_1$, $AA_2$, $AA_3$, $AA_4$, and $AA_5$ is optionally a β aminoacid, an aza-aminoacid or a β-aza-aminoacid;

wherein if the peptide derivative comprises a cysteine, said peptide derivative is optionally a dimer, with the proviso that the peptide is not QRFSR (SEQ ID NO:1), QHNPR (SEQ ID NO:4), QRGPR (SEQ ID NO:3), YQRFSR (SEQ ID NO:9), GlpRFSR (SEQ ID NO:26), CQRFSR (SEQ ID NO:13), GlpHNPK (SEQ ID NO:55) and GlpHNPR (SEQ ID NO:56) in an effective amount to treat pain, wherein the treatment inhibits an activity of a membrane metallo-ectopeptidase selected from the group consisting of NEP and AP-N.

2. The method of claim 1, wherein the peptide derivative has the formula (II):

$$\zeta^a\text{-}Q\text{-}AA^a_2\text{-}AA^a_3\text{-}P\text{-}R\text{-}OH, \quad (II) \text{ (SEQ ID NO: 49)}$$

wherein:

$\zeta^a$ is a hydrogen atom or a Zn chelating group, $AA^a_2$ is R or H, $AA^a_3$ is G, N, F or F(X), F(X) meaning a phenylalanine, the phenyl group of which is substituted by one or more halogen atoms, said Q, $AA^a_2$, $AA^a_3$, P, and R are independently either in the L-configuration or D-configuration, and any one of Q, $AA^a_2$, $AA^a_3$, P, and R is optionally a β aminoacid, an aza-aminoacid or a β-aza-aminoacid;

wherein if the peptide derivative comprises a cysteine, said peptide derivative is optionally a dimer, with the proviso that the peptide is not QHNPR (SEQ ID NO:4) or QRGPR (SEQ ID NO:3).

3. The method of claim 1, wherein the peptide derivative has the formula (III):

$$\zeta^a\text{-}AA''_1\text{-}AA''_2\text{-}AA''_3\text{-}AA''_4\text{-}AA''_5\text{-}OH, \quad (III) \text{ (SEQ ID NO: 50)}$$

wherein:

$\zeta''$ is a hydrogen atom, tyrosine or Y-[linker]-, $AA''_1$ is Q or Glp, $AA''_2$ is K or R, $AA''_3$ is Y, F or F(X), $AA''_4$ is S or S(OAlk), $AA''_5$ is K or R, Y-[linker]- meaning Tyr-[NH—(CH$_2$)$_{n'}$—CO]—, wherein n' is an integer between 1 and 20, F(X) meaning a phenylalanine, the phenyl group of which is substituted by one or more halogen atoms, S(OAlk) meaning a serine, the hydroxyl group of which is substituted by a linear or branched alkanoyl group having from 1 to 20 carbon atoms, said $AA''_1$, $AA''_2$, $AA''_3$, $AA''_4$, and $AA''_5$ are independently either in the L-configuration or D-configuration, and any one of $AA''_1$, $AA''_2$, $AA''_3$, $AA''_4$, and $AA''_5$ is optionally a β aminoacid, an aza-aminoacid or a β-aza-aminoacid;

with the proviso that the peptide is not QRFSR (SEQ ID NO:1), YQRFSR (SEQ ID NO:9) or GlpRFSR (SEQ ID NO:26).

4. The method of claim 1, wherein the peptide derivative has the formula (IV):

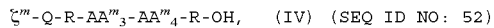
$\zeta''' $-Q-R-$AA'''_3$-$AA'''_4$-R-OH, (IV) (SEQ ID NO: 52)

wherein:
$\zeta'''$ is a hydrogen atom, or a Zn chelating group,
$AA'''_3$ is F or F(X),
$AA'''_4$ is S or S(OAlk),
F(X) meaning a phenylalanine, the phenyl group of which is substituted by one or more halogen atoms,
S(OAlk) meaning a serine, the hydroxyl group of which is substituted by a linear or branched alkanoyl group having from 1 to 20 carbon atoms,
said Q, R, $AA'''_3$, $AA'''_4$, and R are independently either in the L-configuration or D-configuration, and any one of Q, R, $AA'''_3$, $AA'''_4$, and R is optionally β aminoacid, an aza-aminoacid or a β-aza-aminoacid;
wherein if the peptide derivative comprises a cysteine, said peptide derivative is optionally a dimer,
with the proviso that the peptide is not QRFSR (SEQ ID NO:1), YQRFSR (SEQ ID NO:9), or CQRFSR (SEQ ID NO:13).

5. The method of claim 1, wherein the peptide derivative is selected from the group consisting of:
QR—F[4Br]—SR (SEQ ID NO:29), wherein —F[4Br]— is a phenylalanine, the phenyl group of which is substituted in the para position by a bromine atom;
QRFPR (SEQ ID NO:38);
(Acetyl)-QRFSR (SEQ ID NO:5);
C—(—HN—$(CH_2)_8$—CO-)-QRFSR (SEQ ID NO:6);
biotine-(-HN—$(CH_2)_6$—CO-)-QRFSR (SEQ ID NO:7);
dR-dS-dF-dR-dQ (SEQ ID NO:8);
Y—(—HN—$(CH_2)_6$—CO-)-QRFSR (SEQ ID NO:10);
Y—(—HN—$(CH_2)_{12}$—CO-)-QRFSR (SEQ ID NO:11);
QRF—S(O-octanoyl)-R (SEQ ID NO:12);
CQRF—S(O-octanoyl)-R (SEQ ID NO:14);
CQRF—S(O-dodecanoyl)-R (SEQ ID NO:15);
C—(—HN—$(CH_2)_8$—CO-)-QRFSR (SEQ ID NO:16);
C—(—HN—$(CH_2)_{12}$—CO-)-QRFSR (SEQ ID NO:17);
C—(—HN—$(CH_2)_8$—CO-)-QRF—S(O-octanoyl)-R (SEQ ID NO:18);
[Cβ2]QRF—S(O-octanoyl)-R (SEQ ID NO:19);
C—(—HN—$(CH_2)_8$—CO-)-QRFS-[β3R] (SEQ ID NO:20);
C-[dQ]-RF—S(O-octanoyl)-[dR] (SEQ ID NO:21);
C—(—HN—$(CH_2)_8$—CO-)-QRFS-[dR] (SEQ ID NO:22);
[dC]-QRF—S(O-octanoyl)-[dR] (SEQ ID NO:23);
[Cβ2]-QRF—S(O-octanoyl)-[β3R] (SEQ ID NO:24);
[CQRFSR]2 (SEQ ID NO:25);
QRYSR (SEQ ID NO:27);
QR-F[4F]-SR (SEQ ID NO:28), wherein —F[4F]— is a phenylalanine, the phenyl group of which is substituted in the para position by a fluorine atom;
QKFSR (SEQ ID NO:30);
QRFSK (SEQ ID NO:31);
C—(—HN—$(CH_2)_6$—CO-)-QRFSR (SEQ ID NO:32);
C—(—HN—$(CH_2)_6$—CO-)-QRF—S(O-octanoyl)-R (SEQ ID NO:33);
C—(—HN—$(CH_2)_{12}$—CO-)QRF—S(O-octanoyl)-R (SEQ ID NO:34);
C—(—HN—$(CH_2)_{12}$—CO-)-QRFS-dR (SEQ ID NO:35);
C—(—HN—$(CH_2)_{12}$—CO-)-QRF—S(O-octanoyl)-β3R (SEQ ID NO:36);
C—(—HN—$(CH_2)_8$—CO-)-QRF—S(O-octanoyl) β3R (SEQ ID NO:37);
wherein:
Cβ2 is $H_2N$(—$CH_2$—SH)—$CH_2$—CO—;
β3R is —NH—$CH_2$—C[—$(CH_2)_3$—NH—C(NH)($NH_2$)]—COOH;
—S(—O-octanoyl) means a serine, the hydroxyl group of which is substituted by an octanoyl group,
—S(—O-dodecanoyl) means a serine, the hydroxyl group of which is substituted by a dodecanoyl group.

6. The method of claim 1, wherein the Zn chelating group of the peptide derivative is selected in the group consisting of cysteine, C-[linker]-, N-acetyl-cysteine, N-mercaptoacetyl (HS—$CH_2$—CO—), hydroxamic acid (HO—NH—CO—) and an optionally substituted hydroxyquinoline, wherein C-[linker]- is Cys-[NH—$(CH_2)_n$—CO]—, wherein n is an integer between 1 and 20.

7. The method of claim 1, wherein $AA_2$ of the peptide derivative is R.

8. The method of claim 1, wherein $AA_3$ of the peptide derivative is F or F(X).

9. The method of claim 1, wherein $AA_4$ of the peptide derivative is S or S(OAlk).

10. The method of claim 1, wherein $AA_5$ of the peptide derivative is R.

11. The method of claim 2, wherein the Zn chelating group of the peptide derivative is selected from the group consisting of cysteine, C-[linker]-, N-acetyl-cysteine, N-mercaptoacetyl (HS—$CH_2$—CO—), hydroxamic acid (HO—NH—CO—) and an optionally substituted hydroxyquinoline, wherein C-[linker]- is Cys-[NH—$(CH_2)_n$—CO]—, wherein n is an integer between 1 and 20.

12. The method of claim 1, wherein the pain is chronic, acute, visceral inflammatory or neuropathic pain.

13. The method of claim 1, wherein said pain is acute pain or chronic pain.

14. The method of claim 1, wherein said pain is a chronic inflammatory pain selected from the group consisting of arthritis pain, visceral inflammatory pain, inflammatory bowel disease pain, post-operative injury pain, and neuropathic pain.

15. The method of claim 1, wherein said pain is neuropathic pain.

16. The method of claim 15, wherein the neuropathic pain has resulted from cancer and/or cancer therapy.

17. The method of claim 4, wherein the Zn chelating group of the peptide derivative is selected from the group consisting of cysteine, C-[linker]-, N-acetyl-cysteine, N-mercaptoacetyl (HS—$CH_2$—CO—), hydroxamic acid (HO—NH—CO—) and an optionally substituted hydroxyquinoline, wherein C-[linker]- is Cys-[NH—$(CH_2)_n$—CO]—, wherein n is an integer between 1 and 20.

* * * * *

```
SEQUENCE LISTING

<160> NUMBER OF SEQ ID NOS: 54

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gln Arg Phe Ser Arg
1               5

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: C-term amidated

<400> SEQUENCE: 2

Gln Arg Phe Ser Arg
1               5
```

```
<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Arg Gly Pro Arg
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gln His Asn Pro Arg
1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term acetylated

<400> SEQUENCE: 5

Gln Arg Phe Ser Arg
1               5

<210> SEQ ID NO 6
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term-(-HN-(CH2)8-CO)

<400> SEQUENCE: 6

Gln Arg Phe Ser Arg
1               5

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: N-term biotine-(-HN-(CH2)6-CO-)
```

```
<400> SEQUENCE: 7

Gln Arg Phe Ser Arg
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-Arg
<220> FEATURE:
<221> NAME/KEY: MOD_RES
<222> LOCATION: (2)..(2)
<223> OTHER INFORMATION: D-Ser
<220> FEATURE:
<221> NAME/KEY: MOD_RES
<222> LOCATION: (3)..(3)
<223> OTHER INFORMATION: D-Phe
<220> FEATURE:
<221> NAME/KEY: MOD_RES
<222> LOCATION: (4)..(4)
<223> OTHER INFORMATION: D-Arg
<220> FEATURE:
<221> NAME/KEY: MOD_RES
<222> LOCATION: (5)..(5)
<223> OTHER INFORMATION: D-Gln

<400> SEQUENCE: 8

Arg Ser Phe Arg Gln
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Gln Arg Phe Ser Arg
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr-(-HN-(CH2)6-CO-)

<400> SEQUENCE: 10

Tyr Gln Arg Phe Ser Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Tyr-(-HN-(CH2)12-CO-)

<400> SEQUENCE: 11

Tyr Gln Arg Phe Ser Arg
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser(O-octanoyl)

<400> SEQUENCE: 12

Gln Arg Phe Ser Arg
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Cys Gln Arg Phe Ser Arg
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser(O-octanoyl)

<400> SEQUENCE: 14

Cys Gln Arg Phe Ser Arg
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser(O-dodecanoyl)

<400> SEQUENCE: 15

Cys Gln Arg Phe Ser Arg
1               5
```

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)8-CO-)

<400> SEQUENCE: 16

Cys Gln Arg Phe Ser Arg
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)12-CO-)

<400> SEQUENCE: 17

Cys Gln Arg Phe Ser Arg
1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)8-CO-)
<220> FEATURE:
<221> NAME/KEY: MOD_RES
<222> LOCATION: (5)..(5)
<223> OTHER INFORMATION: Ser(O-octanoyl)

<400> SEQUENCE: 18

Cys Gln Arg Phe Ser Arg
1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-H2N(-CH2-SH)-CH2-CO-
<220> FEATURE:
<221> NAME/KEY: MOD_RES
<222> LOCATION: (5)..(5)
<223> OTHER INFORMATION: Ser(O-octanoyl)

<400> SEQUENCE: 19

Cys Gln Arg Phe Ser Arg
1               5
```

```
<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)8-CO-)
<220> FEATURE:
<221> NAME/KEY: MOD_RES
<222> LOCATION: (6)..(6)
<223> OTHER INFORMATION: Arg-NH-CH2-C[-(CH2)3-NH-C(NH)(NH2)]-COOH

<400> SEQUENCE: 20

Cys Gln Arg Phe Ser Arg
1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Gln
<220> FEATURE:
<221> NAME/KEY: MOD_RES
<222> LOCATION: (5)..(5)
<223> OTHER INFORMATION: Ser(O-octanoyl)
<220> FEATURE:
<221> NAME/KEY: MOD_RES
<222> LOCATION: (6)..(6)
<223> OTHER INFORMATION: D-Arg

<400> SEQUENCE: 21

Cys Gln Arg Phe Ser Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)8-CO-)
<220> FEATURE:
<221> NAME/KEY: MOD_RES
<222> LOCATION: (6)..(6)
<223> OTHER INFORMATION: D-Arg

<400> SEQUENCE: 22

Cys Gln Arg Phe Ser Arg
1               5

<210> SEQ ID NO 23
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(1)
<223> OTHER INFORMATION: D-Cys
<220> FEATURE:
<221> NAME/KEY: MOD_RES
<222> LOCATION: (5)..(5)
<223> OTHER INFORMATION: Ser(O-octanoyl)
<220> FEATURE:
<221> NAME/KEY: MOD_RES
<222> LOCATION: (6)..(6)
<223> OTHER INFORMATION: D-Arg

<400> SEQUENCE: 23

Cys Gln Arg Phe Ser Arg
1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-H2N(-CH2-SH)-CH2-CO-
<220> FEATURE:
<221> NAME/KEY: MOD_RES
<222> LOCATION: (5)..(5)
<223> OTHER INFORMATION: Ser(O-octanoyl)
<220> FEATURE:
<221> NAME/KEY: MOD_RES
<222> LOCATION: (6)..(6)
<223> OTHER INFORMATION: Arg-NH-CH2-C[-(CH2)3-NH-C(NH)(NH2)]-COOH

<400> SEQUENCE: 24

Cys Gln Arg Phe Ser Arg
1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: DISULFID
<222> LOCATION: (1)..(6)

<400> SEQUENCE: 25

Cys Gln Arg Phe Ser Arg
1               5

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Pyroglutamate

<400> SEQUENCE: 26

Glu Arg Phe Ser Arg
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gln Arg Tyr Ser Arg
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe[4F]

<400> SEQUENCE: 28

Gln Arg Phe Ser Arg
1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Phe[4Br]

<400> SEQUENCE: 29

Gln Arg Phe Ser Arg
1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Lys Phe Ser Arg
1               5

<210> SEQ ID NO 31
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Arg Phe Ser Lys
1               5

<210> SEQ ID NO 32
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)6-CO-)

<400> SEQUENCE: 32

Cys Gln Arg Phe Ser Arg
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)6-CO-)
<220> FEATURE:
<221> NAME/KEY: MOD_RES
<222> LOCATION: (5)..(5)
<223> OTHER INFORMATION: Ser(O-octanoyl)

<400> SEQUENCE: 33

Cys Gln Arg Phe Ser Arg
1               5

<210> SEQ ID NO 34
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)12-CO-)
<220> FEATURE:
<221> NAME/KEY: MOD_RES
<222> LOCATION: (5)..(5)
<223> OTHER INFORMATION: Ser(O-octanoyl)

<400> SEQUENCE: 34

Cys Gln Arg Phe Ser Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)12-CO-)
<220> FEATURE:
<221> NAME/KEY: MOD_RES
<222> LOCATION: (6)..(6)
<223> OTHER INFORMATION: D-Arg

<400> SEQUENCE: 35
```

```
Cys Gln Arg Phe Ser Arg
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)12-CO-)
<220> FEATURE:
<221> NAME/KEY: MOD_RES
<222> LOCATION: (5)..(5)
<223> OTHER INFORMATION: Ser(O-octanoyl)
<220> FEATURE:
<221> NAME/KEY: MOD_RES
<222> LOCATION: (6)..(6)
<223> OTHER INFORMATION: Arg-NH-CH2-C[-(CH2)3-NH-C(NH)(NH2)]-COOH

<400> SEQUENCE: 36

Cys Gln Arg Phe Ser Arg
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-(-HN-(CH2)8-CO-)
<220> FEATURE:
<221> NAME/KEY: MOD_RES
<222> LOCATION: (5)..(5)
<223> OTHER INFORMATION: Ser(O-octanoyl)
<220> FEATURE:
<221> NAME/KEY: MOD_RES
<222> LOCATION: (6)..(6)
<223> OTHER INFORMATION: Arg-NH-CH2-C[-(CH2)3-NH-C(NH)(NH2)]-COOH

<400> SEQUENCE: 37

Cys Gln Arg Phe Ser Arg
1               5

<210> SEQ ID NO 38
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Arg Phe Pro Arg
1               5

<210> SEQ ID NO 39
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (3)..(3)
<223> OTHER INFORMATION: Phenyl group is substituted by one or more
      halogen atoms

<400> SEQUENCE: 39

Gln Arg Phe Ser Arg
1               5

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abz
<220> FEATURE:
<221> NAME/KEY: MOD_RES
<222> LOCATION: (5)..(5)
<223> OTHER INFORMATION: Lys-Dnp-OH

<400> SEQUENCE: 40

Xaa Arg Gly Phe Lys
1               5

<210> SEQ ID NO 41
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Mca-Arg
<220> FEATURE:
<221> NAME/KEY: MOD_RES
<222> LOCATION: (9)..(9)
<223> OTHER INFORMATION: Lys-Dnp-OH

<400> SEQUENCE: 41

Arg Pro Pro Gly Phe Ser Ala Phe Lys
1               5

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Abz
<220> FEATURE:
<221> NAME/KEY: MOD_RES
<222> LOCATION: (2)..(2)
<223> OTHER INFORMATION: D-Arg
<220> FEATURE:
<221> NAME/KEY: MOD_RES
<222> LOCATION: (4)..(4)
<223> OTHER INFORMATION: Leu-EDDnp

<400> SEQUENCE: 42

Xaa Arg Gly Leu
1
```

```
<210> SEQ ID NO 43
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: May or may not be present
<220> FEATURE:
<221> NAME/KEY: MOD_RES
<222> LOCATION: (2)..(2)
<223> OTHER INFORMATION: Gln or Glp
<220> FEATURE:
<223> OTHER INFORMATION: see specification as filed for detailed
      description of substitutions and preferred embodiments

<400> SEQUENCE: 43

Tyr Xaa Arg Phe Ser Arg
1               5

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Tyr-[linker]-, a Zn chelating group such
      as Cys, Cys-[linker]- or N-acetyl-Cys or absent
<220> FEATURE:
<221> NAME/KEY: MOD_RES
<222> LOCATION: (2)..(2)
<223> OTHER INFORMATION: Gln or Glp
<220> FEATURE:
<221> NAME/KEY: MOD_RES
<222> LOCATION: (3)..(3)
<223> OTHER INFORMATION: Lys, Arg or His
<220> FEATURE:
<221> NAME/KEY: MOD_RES
<222> LOCATION: (4)..(4)
<223> OTHER INFORMATION: Tyr, Gly, Asn, Phe or Phe(X), wherein X
      designates the phenyl group is substituted by one or more halogen
      atoms
<220> FEATURE:
<221> NAME/KEY: MOD_RES
<222> LOCATION: (5)..(5)
<223> OTHER INFORMATION: Pro, Ser or Ser(OAlk)
<220> FEATURE:
<221> NAME/KEY: MOD_RES
<222> LOCATION: (6)..(6)
<223> OTHER INFORMATION: Lys or Arg
<220> FEATURE:
<223> OTHER INFORMATION: see specification as filed for detailed
      description of substitutions and preferred embodiments

<400> SEQUENCE: 44

Xaa Xaa Xaa Xaa Xaa Xaa
1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)..(1)
<223> OTHER INFORMATION: Gln or Glp
<220> FEATURE:
<221> NAME/KEY: MOD_RES
<222> LOCATION: (2)..(2)
<223> OTHER INFORMATION: Lys, Arg or His
<220> FEATURE:
<221> NAME/KEY: MOD_RES
<222> LOCATION: (3)..(3)
<223> OTHER INFORMATION: Tyr, Gly, Asn, Phe or Phe(X), wherein X
      designates the phenyl group is substituted by one or more halogen
      atoms
<220> FEATURE:
<221> NAME/KEY: MOD_RES
<222> LOCATION: (4)..(4)
<223> OTHER INFORMATION: Pro, Ser or Ser(OAlk)
<220> FEATURE:
<221> NAME/KEY: MOD_RES
<222> LOCATION: (5)..(5)
<223> OTHER INFORMATION: Lys or Arg
<220> FEATURE:
<223> OTHER INFORMATION: see specification as filed for detailed
      description of substitutions and preferred embodiments

<400> SEQUENCE: 45

Xaa Xaa Xaa Xaa Xaa
1               5

<210> SEQ ID NO 46
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser(OAlk)

<400> SEQUENCE: 46

Gln Arg Phe Ser Arg
1               5

<210> SEQ ID NO 47
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-[linker]

<400> SEQUENCE: 47

Cys Gln Arg Phe Ser Arg
1               5

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Cys-[NH-(CH2)6-CO-]
<220> FEATURE:
<221> NAME/KEY: MOD_RES
```

```
<222> LOCATION: (5)..(5)
<223> OTHER INFORMATION: Ser(OAlk)

<400> SEQUENCE: 48

Cys Gln Arg Phe Ser Arg
1               5

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A Zn chelating group such as Cys, Cys-[linker]-
      or N-acetyl-Cys or absent
<220> FEATURE:
<221> NAME/KEY: MOD_RES
<222> LOCATION: (3)..(3)
<223> OTHER INFORMATION: Arg or His
<220> FEATURE:
<221> NAME/KEY: MOD_RES
<222> LOCATION: (4)..(4)
<223> OTHER INFORMATION: Gly, Asn, Phe or Phe(X), wherein X designates
      the phenyl group is substituted by one or more halogen atoms
<220> FEATURE:
<223> OTHER INFORMATION: see specification as filed for detailed
      description of substitutions and preferred embodiments

<400> SEQUENCE: 49

Xaa Gln Xaa Xaa Pro Arg
1               5

<210> SEQ ID NO 50
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Tyr, Tyr-[linker]- or absent
<220> FEATURE:
<221> NAME/KEY: MOD_RES
<222> LOCATION: (2)..(2)
<223> OTHER INFORMATION: Gln or Glp
<220> FEATURE:
<221> NAME/KEY: MOD_RES
<222> LOCATION: (3)..(3)
<223> OTHER INFORMATION: Lys or Arg
<220> FEATURE:
<221> NAME/KEY: MOD_RES
<222> LOCATION: (4)..(4)
<223> OTHER INFORMATION: Tyr, Phe or Phe(X), wherein X designates the
      phenyl group is substituted by one or more halogen atoms
<220> FEATURE:
<221> NAME/KEY: MOD_RES
<222> LOCATION: (5)..(5)
<223> OTHER INFORMATION: Ser or Ser(OAlk)
<220> FEATURE:
<221> NAME/KEY: MOD_RES
<222> LOCATION: (6)..(6)
<223> OTHER INFORMATION: Lys or Arg
<220> FEATURE:
<223> OTHER INFORMATION: see specification as filed for detailed
      description of substitutions and preferred embodiments
```

```
<400> SEQUENCE: 50

Tyr Xaa Xaa Xaa Xaa
1               5

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Glp
<220> FEATURE:
<221> NAME/KEY: MOD_RES
<222> LOCATION: (3)..(3)
<223> OTHER INFORMATION: Phe or Phe(X), wherein X designates the phenyl
      group is substituted by one or more halogen atoms
<220> FEATURE:
<221> NAME/KEY: MOD_RES
<222> LOCATION: (4)..(4)
<223> OTHER INFORMATION: Ser(OAlk)
<220> FEATURE:
<221> NAME/KEY: MOD_RES
<222> LOCATION: (5)..(5)
<223> OTHER INFORMATION: Lys or Arg
<220> FEATURE:
<223> OTHER INFORMATION: see specification as filed for detailed
      description of substitutions and preferred embodiments

<400> SEQUENCE: 51

Xaa Arg Xaa Ser Xaa
1               5

<210> SEQ ID NO 52
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A Zn chelating group such as Cys, Cys-[linker]-
      or N-acetyl-Cys or absent
<220> FEATURE:
<221> NAME/KEY: MOD_RES
<222> LOCATION: (4)..(4)
<223> OTHER INFORMATION: Phe or Phe(X), wherein X designates the phenyl
      group is substituted by one or more halogen atoms
<220> FEATURE:
<221> NAME/KEY: MOD_RES
<222> LOCATION: (5)..(5)
<223> OTHER INFORMATION: Ser or Ser(OAlk)
<220> FEATURE:
<223> OTHER INFORMATION: see specification as filed for detailed
      description of substitutions and preferred embodiments

<400> SEQUENCE: 52

Xaa Gln Arg Xaa Xaa Arg
1               5

<210> SEQ ID NO 53
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)..(1)
<223> OTHER INFORMATION: Cys-[linker]
<220> FEATURE:
<221> NAME/KEY: MOD_RES
<222> LOCATION: (5)..(5)
<223> OTHER INFORMATION: Ser(O-octanoyl)

<400> SEQUENCE: 53

Cys Gln Arg Phe Ser Arg
1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gln Arg Phe Thr Arg
1               5
```